United States Patent
Alexandrov et al.

(10) Patent No.: US 7,691,991 B2
(45) Date of Patent: *Apr. 6, 2010

(54) SEQUENCE-DETERMINED DNA FRAGMENTS ENCODING CYTOCHROME P450 PROTEINS

(75) Inventors: Nickolai Alexandrov, Thousand Oaks, CA (US); Vyacheslav Brover, Simi Valley, CA (US); Kenneth Feldmann, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/362,546

(22) Filed: Feb. 24, 2006

(65) Prior Publication Data

US 2006/0235217 A1 Oct. 19, 2006

Related U.S. Application Data

(63) Continuation-in-part of application No. 11/006,231, filed on Dec. 6, 2004, which is a continuation of application No. 10/645,822, filed on Aug. 22, 2003, which is a continuation-in-part of application No. 10/216,621, filed on Aug. 12, 2002, now abandoned, which is a continuation of application No. 09/940,257, filed on Aug. 24, 2001, now abandoned, which is a continuation-in-part of application No. 09/832,192, filed on Apr. 11, 2001, now abandoned, said application No. 10/645,822 is a continuation-in-part of application No. 10/461,476, filed on Jun. 16, 2003, now abandoned, which is a continuation of application No. 10/191,406, filed on Jul. 10, 2002, now abandoned, which is a continuation of application No. 09/940,255, filed on Aug. 24, 2001, now abandoned, which is a continuation-in-part of application No. 09/832,192, said application No. 10/645,822 is a continuation-in-part of application No. 10/282,058, filed on Oct. 29, 2002, now abandoned, which is a continuation-in-part of application No. 10/162,726, filed on Jun. 6, 2002, which is a continuation-in-part of application No. 09/832,192, and a continuation-in-part of application No. 09/940,258, filed on Aug. 24, 2001, now abandoned, which is a continuation-in-part of application No. 09/832,192.

(60) Provisional application No. 60/197,870, filed on Apr. 17, 2000.

(51) Int. Cl.
C07H 21/04 (2006.01)

(52) U.S. Cl. .................................... 536/23.2

(58) Field of Classification Search ................. 530/350
See application file for complete search history.

(56) References Cited

U.S. PATENT DOCUMENTS

| | | |
|---|---|---|
| 4,801,540 A | 1/1989 | Hiatt et al. |
| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,283,184 A | 2/1994 | Jorgensen et al. |
| 5,410,270 A | 4/1995 | Rybicki et al. |
| 5,445,943 A | 8/1995 | Hoenes et al. |
| 5,538,880 A | 7/1996 | Lundquist et al. |
| 5,591,616 A | 1/1997 | Hiei et al. |
| 5,723,766 A | 3/1998 | Theologis et al. |
| 5,766,847 A | 6/1998 | Jackle et al. |
| 5,859,330 A | 1/1999 | Bestwick et al. |
| 6,004,804 A | 12/1999 | Kumar et al. |
| 6,010,907 A | 1/2000 | Kmiec et al. |
| 6,329,571 B1 | 12/2001 | Hiei |
| 6,423,885 B1 | 7/2002 | Waterhouse et al. |
| 2005/0009187 A1 | 1/2005 | Shinozaki et al. |
| 2005/0246785 A1 | 11/2005 | Cook et al. |
| 2006/0041952 A1 | 2/2006 | Cook |
| 2006/0059582 A1 | 3/2006 | Jankowski et al. |
| 2006/0059585 A1 | 3/2006 | Jankowski et al. |

FOREIGN PATENT DOCUMENTS

EP    1 033 405    6/2000

(Continued)

OTHER PUBLICATIONS

Nakamura et al., Structural Analysis of *Arabidopsis thaliana* Chromosome 3. I. Sequnce features of the Regions of 4,504,864 bp Covered by Sixty P1 and TAC Clones, DNA Research, 7 (2000), p. 131-135.*

(Continued)

*Primary Examiner*—Anand U Desai
(74) *Attorney, Agent, or Firm*—Fish & Richardson P.C.

(57) ABSTRACT

The present invention provides DNA molecules that constitute fragments of the genome of a plant, and polypeptides encoded thereby. The DNA molecules are useful for specifying a gene product in cells, either as a promoter or as a protein coding sequence or as an UTR or as a 3' termination sequence, and are also useful in controlling the behavior of a gene in the chromosome, in controlling the expression of a gene or as tools for genetic mapping, recognizing or isolating identical or related DNA fragments, or identification of a particular individual organism, or for clustering of a group of organisms with a common trait.

1 Claim, No Drawings

FOREIGN PATENT DOCUMENTS

| WO | WO95/35505 | 12/1995 |
|----|------------|---------|
| WO | WO 98/07842 | 2/1998 |
| WO | WO 99/32619 | 1/1999 |
| WO | WO99/07865 | 2/1999 |
| WO | WO99/58723 | 11/1999 |
| WO | WO 01/35725 | 5/2001 |
| WO | WO 01/75164 | 10/2001 |
| WO | WO 02/15675 | 2/2002 |
| WO | WO 02/46449 | 6/2002 |
| WO | WO 03/013227 | 2/2003 |
| WO | WO 03044190 | 5/2003 |
| WO | WO 2004/035798 | 4/2004 |
| WO | WO 2006/005023 | 1/2006 |

OTHER PUBLICATIONS

Score Search Results Details, for Seq ID No. 2, See Result 1, pp. 1-3.*
NCBI sequence printout, pp. 1-2.*
GenCore version 6.2 sequence printout, pp. 1-6.*
Guengerich, F.P., "Common and Uncommon Cytochrome P450 Reactions Related to Metabolism and Chemical Toxicity", Chem. Res. Toxicol. 14(6): 611-650 (May 2001).*
Office Action from U.S. Appl. No. 11/367,760, document dated Apr. 10, 2007, 26 pages; Jul. 10, 2007 Response to Office Action dated Apr. 10, 2007, 10 pages.
Office Action from U.S. Appl. No. 11/368,321, document dated Aug. 29, 2007, 4 pages.
Final Office Action from U.S. Appl. No. 11/357,357, dated Nov. 29, 2007, 9 pages.
Final Office Action from U.S. Appl. No. 11/180,418, dated Nov. 30, 2007, 10 pages.
Office Action from U.S. Appl. No. 11/370,253, dated Oct. 30, 2007, 20 pages.
Office Action from U.S. Appl. No. 11/371,356, dated Oct. 30, 2007, 20 pages.
Office Action from U.S. Appl. No. 11/371,624, dated Oct. 31, 2007, 21 pages.
Office Action from U.S. Appl. No. 11/396,357, dated Nov. 7, 2007, 7 pages.
Office Action from U.S. Appl. No. 11/371,623, dated Nov. 16, 2007, 10 pages.
Office Action from U.S. Appl. No. 11/369,168, dated Oct. 30, 2007, 20 pages.
Notice of Allowance from U.S. Appl. No. 11/367,760, dated Oct. 5, 2007, 6 pages.
Notice of Allowance from U.S. Appl. No. 11/153,185, dated Nov. 13, 2007, 7 pages.
Notice of Allowance from U.S. Appl. No. 11/372,369, dated Nov. 13, 2007, 7 pages.
Notice of Allowance from U.S. Appl. No. 11/396,378, dated Nov. 13, 2007, 7 pages.
Response to Office Action from U.S. Appl. No. 11/368,321, filed Nov. 29, 2007, 5 pages.
Notice of Allowance from U.S. Appl. No. 11/358,685, dated Dec. 21, 2007, 4 pages.
Notice of Allowance from U.S. Appl. No. 11/357,747, dated Dec. 21, 2007, 4 pages.
Notice of Allowance from U.S. Appl. No. 11/357,909, dated Dec. 21, 2007, 4 pages.
Notice of Allowance from U.S. Appl. No. 11/368,321, dated Dec. 21, 2007, 4 pages.
Final Office Action from U.S. Appl. No. 11/369,173, dated May 3, 2007, 9 pages.
Notice of Allowance from U.S. Appl. No. 11/362,546, dated Jan. 23, 2008, 6 pages.
Notice of Allowance from U.S. Appl. No. 11/357,760, dated Feb. 28, 2008, 4 pages.
Response to Final Office Action from U.S. Appl. No. 11/180,418, filed Jan. 30, 2008, 5 pages.
Response to Office Action from U.S. Appl. No. 11/369,168, filed Jan. 30, 2008, 7 pages.
Response to Office Action from U.S. Appl. No. 11/370,253, filed Jan. 30, 2008, 7 pages.
Response to Office Action from U.S. Appl. No. 11/371,356, filed Jan. 30, 2008, 7 pages.
Response to Office Action from U.S. Appl. No. 11/371,624, filed Jan. 30, 2008, 8 pages.
Response to Office Action from U.S. Appl. No. 11/371,623, filed Feb. 15, 2008, 4 pages.
Alexandrov et al., "Features of *Arabidopsis genees* and genome discovered using full-length cDNAs" *Plant Molecular Biology*, 60(1):69-85 (2006).
Broun et al. "Catlytic plasticity of fatty acid modification enzymes underlying chemical diversity of plant lipids" *Science*, 282(13):1315-1317 (1998).
Doerks et al. "Protein annotation: Detective work for function prediction" *TIG*, 14(6):248-250 (1998).
Galweiler et al. "Techincal advance: the DNA-binding activity of gal4 is inhibited by methylation of the gal4 binding site in plant chromatin" *Plant Journal*, 23(1):143-157 (2000).
Haas et al. "Full-length messenger RNA sequences greatly improve genome annotation" *Genome Biology*, 3:1-12 (2002).
Lazar et al. "Transforming growth factor a: Mutation of aspartic acid 47 and leucine 48 in different biological activities" *Molecular & Cell Biology*, 8(3):1247-1252 (1988).
Office Action from U.S. Appl. No. 11/153,185, document dated Dec. 28, 2006, 5 pages; Mar. 28, 2007 Response to Office Action dated Dec. 28, 2006, 16 pages; Notice of Allowance from U.S. Appl. No. 11/153,185, dated Jun. 19, 2007.
Office Action from U.S. Appl. No. 11/180,101, document dated Dec. 28, 2006, 5 pages; Mar. 28, 2007 Response to Office Action dated Dec. 28, 2006, 15 pages; Notice of Allowance from U.S. Appl. No. 11/180,101, dated Jun. 19, 2007.
Office Action from U.S. Appl. No. 11/180,418, document dated May 17, 2007, 11 pages; Sep. 17, 2007 Response to Office Action dated May 17, 2007, 8 pages.
Office Action from U.S. Appl. No. 11/362,437, document dated Apr. 9, 2007, 15 pages; Jul. 9, 2007 Response to Office Action dated Apr. 9, 2007, 7 pages; Notice of Allowance from U.S. Appl. No. 11/362,437, dated Aug. 9, 2007.
Office Action from U.S. Appl. No. 11/358,685, document dated Apr. 5, 2007, 6 pages; Aug. 3, 2007 Response to Office Action dated Apr. 5, 2007, 7 pages.
Office Action from U.S. Appl. No. 11/357,909, document dated Apr. 9, 2007, 5 pages; Jul. 9, 2007 Response to Office Action dated Apr. 9, 2007, 6 pages.
Office Action from U.S. Appl. No. 11/357,357, document dated May 17, 2007, 9 pages; Sep. 17, 2007 Response to Office Action dated May 17, 2007, 6 pages.
Office Action from U.S. Appl. No. 11/357,747, document dated Apr. 9, 2007, 20 pages; Aug. 3, 2007 Response to Office Action dated Apr. 9, 2007, 8 pages.
Office Action from U.S. Appl. No. 11/368,322, document dated Apr. 4, 2007, 25 pages.
Office Action from U.S. Appl. No. 11/368,321, document dated Aug. 29, 2007, 9 pages.
Office Action from U.S. Appl. No. 11/369,193, document dated Nov. 15, 2006, 7 pages; Feb. 14, 2007 Response to Office Action dated Nov. 15, 2006, 5 pages.
Office Action from U.S. Appl. No. 11/369,173, document dated Nov. 15, 2006, 14 pages; Feb. 14, 2007 Response to Office Action dated Nov. 15, 2006, 8 pages.
Office Action from U.S. Appl. No. 11/369,173, document dated May 3, 2007, 15 pages.
Office Action from U.S. Appl. No. 11/370,240, document dated Sep. 27, 2007, 8 pages.
Office Action from U.S. Appl. No. 11/372,369, document dated Apr. 5, 2007, 18 pages; Jul. 5, 2007 Response to Office Action dated Apr. 5, 2007, 7 pages; Notice of Allowance from U.S. Appl. No. 11/372,369, dated Aug. 23, 2007.
Office Action from U.S. Appl. No. 11/396,378, document dated May 2, 2007, 14 pages; Aug. 2, 2007 Response to Office Action dated May 2, 2007, 4 pages; Notice of Allowance from U.S. Appl. No. 11/396,378, dated Sep. 26, 2007.

Office Action from U.S. Appl. No. 11/396,457, document dated May 7, 2007, 11 pages; Jul. 2, 2007 Response to Office Action dated May 2, 2007, 4 pages; Notice of Allowance from U.S. Appl. No. 11/396,457, dated Sep. 24, 2007.
U.S. Appl. No. 60/121,700, filed Feb. 25, 1999, Bouckaert et al.
GenBank Accession No. CAA16567 dated Nov. 14, 2006, 2 pages.
GenBank Accession No. CAA19798 dated Nov. 14, 2006, 2 pages.
GenBank Accession No. CAB79237 dated Nov. 14, 2006, 2 pages.
GenBank Accession No. AAN72006 dated Nov. 19, 2002, 2 pages.
GenBank Accession No. AAP21371 dated Apr. 25, 2003, 2 pages.
GenBank Accession No. Q9LTM2 dated Nov. 28, 2006, 2 pages.
GenBank Accession No. Q9LTM1 dated Nov. 28, 2006, 3 pages.
GanBank Accession No. BAB02441 dated Feb. 14, 2004, 2 pages.
GenBank Accession No. BAB02440 dated Feb. 14, 2004, 2 pages.
GenBank Accession No. AAK25981 dated Sep. 18, 2002, 2 pages.
GenBank Accession No. AAK64138 dated Sep. 18, 2002, 2 pages.
GenBank Accession No. NP 004553, dated Feb. 11, 2007.
GenBank Accession No. NP 194013 dated Jun. 9, 2006, 2 pages.
GenBank Accession No. NP 974594 dated Jun. 9, 2006, 2 pages.
GenBank Accession No. NP 189251 dated Jun. 9, 2006, 2 pages.
GenBank Accession No. NP 189250 dated Jun. 9, 2006, 2 pages.
URL:http://sanger.ac.uk/Pfam.
URL:http://genome.wustl.edu/Pfam/.
URL:http://www.ncbi.nlm.nih.gov/UniGene/clust.cgi?ORG=At&CID=5693.
Ahn et al., "Homoeologous relationship of rice, wheat and maize chromosomes" *Molecular and General Genetics*, 241:483-90 (1993).
Albert et al., "Site-specific integration of DNA into wild-type and mutant lox site placed in the plant genome" *The Plant Journal*, 7:649 (1995).
Alonso-Blanco et al. (Methods in Molecular Biology, vol. 82, "*Arabidopsis* Protocols", pp. 137-146. J.M. Martinez-Zapater and J. Salinas, eds., c. 1998 by *Humana Press*, Totowa, NJ).
*Arabidopsis* P450 Gene Family. Retrieved from the Internet: URL:http://www.arabidopsis.org/info/genefamily/p450.html, dated Jul. 29, 2004.
*Arabidopsis thaliana*—MTC11.11 / At3g26200. Retrieved from the Internet: URL:http://www.tigr.org/tigr-scripts/euk_manatee/shared/ORF_infopage.cgi?db=athl&orf=At3g.
Armaleo, et al., "Biolistic nuclear transformation of *Saccharomyces cerevisiae* and other fungi" *Current Genetics*, 17:97 (1990).
AtMYB23 MYB transcription factor target down-regulation; Jul. 6, 2004. Retrieved from the Internet: URL:http://www.ncbi.nlm.nih.gov/projects/geo/gds/gds_browse.cgi?gds=694, document undated.
Ausubel et al. (Current Protocols in Molecular Biology, *Greene Publishing*, New York (1992).
Azpiroz-Leehan et al., "T-DNA insertion mutagenesis in *Arabidopsis*: going back and forth" *Trends in Genetics*, 13:152 (1997).
Baerson, et al., "Developmental regulation of an acyl carrier protein gene promoter in vegetative and reproductive tissues" *Plant Molecular Biology*, 22(2), pp. 255-267 (1993).
Bateman, et al., "Pfam 3.1: 1313 multiple alignments and profile HMMs match the majority of proteins" *Nucleic Acids Research*, vol. 27, (1999), pp. 260-262.
Bechtold, et al., "In planta Agrobacterium mediated gene transfer by infiltration of adult *Arabidopsis thaliana* plants" *C.R. Acad. Sci. Paris*, 316, pp. 1194-1199 (1993).
Bonner et al., "Reduction in the Rate of DNA reassociation by Sequence Divergence" *J. Mol. Biol.*, 81:123 (1973).
Bradshaw et al., "A new vector for recombination-based cloning of large DNA fragments from yeast artificial chromosomes" *Nucl. Acids. Res.*, 23:4850-4856 (1995).
Brummell, et al., Inverted repeat of a heterologous 3'-untranslated region for high-efficiency, high-throughput gene silencing; *The Plant Journal*, 33, pp. 793-800 (2003).
Burke et al., "Cloning of large segments of exogenous DNA into yeast by means of artificial chromosome vectors" *Science*, 236:806-812 (1987).

Burr ("Mapping Genes with Recombinant Inbreds", pp. 249-254. In Freeling, M. and V. Walbot (Ed.), The Maize Handbook, c. 1994 by Springer-Verlag New York, Inc.: New York, NY, USA; Berlin Germany.
Burr et al., "Gene mapping with recombinant inbreds in maize" *Genetics*, 118:519 (1998).
Bustos, et al., "Regulation of β-Glucuronidase Expression in Transgenic Tobacco Plants by an A/T-Rich, cis-Acting Sequence Found Upstream of a French Bean β-Phaseolin Gene" *The Plant Cell*, vol. 1, pp. 839-853 (1989).
Carels et al., "Compositional properties of homologous coding sequences from plants" *J. Mol. Evol.*, 46:45 (1998).
Cerdan, et al., A 146 bp fragment of the tobacco Lhcb1*2 promoter confers very-low-fluence, low-fluence and high-irradiance responses of phytochrome to a minimal CaMV 35S promoter, Plant *Molecular Biology*, 33, pp. 245-255 (1997).
Chen, et al., "Functional analysis of regulatory elements in a plant embryo-specific gene" *Proc. Natl. Acad. Sci. USA*, vol. 83, pp. 8560-8564 (1986).
Christou, "Strategies for variety-independent genetic transformation of important cereals, legumes and woody species utilizing particle bombardment" *Euphytica*, 85(1-3):13-27, (1995).
Conkling, et al., "Isolation of transcriptionally regulated root-specific genes from tobacco" *Plant Physiol.*, 93:1203-1211 (1990).
De Feyter, et al., "Expressing Ribozymes in Plants; Methods in Molecular Biology" vol. 74, Chapter 43 (Edited by Turner, P.C., *Humana Press Inc.*, Totowa, NJ).
De Martinis et al., "Silencing gene expression of the ethylene-forming enzyme results in a reversible inhibition of ovule development in transgenic tobacco plants" *Plant Cell*, 11:1061 (1999).
deVicente and Tanksley "QTL analysis of transgressive segregation in an interspecific tomato cross" *Genetics*, 134:585 (1993).
Escudero, et al., "T-DNA transfer in meristematic cells of maize provided with intracellular Agrobacterium" *The Plant Journal*, 10(2), pp. 355-560 (1996).
Evans et al., Protoplasts Isolation and Culture in "Handbook of Plant Cell Culture," pp. 124 176, *MacMillan Publishing Company*, New York, 1983.
Fejes, et al., "A 268 bp upstream sequence mediates the circadian clock-regulated transcription of the wheat Cab-1 gene in transgenic plants" *Plant Molecular Biology*, 15, pp. 921-932 (1990).
Fennoy et al. "Synonymous codon usage in *Zea mays* L. nuclear genes is varied by levels of C and G-ending codons" *Nucleic Acids Research*, 21(23):5294 (1993).
Frischauf et al., "Lambda replacement vectors carrying polylinker sequences" *J. Mol. Biol.*, 170:827-842 (1983).
Fromm et al. "Expression of genes transferred into monocot and dicot plant cells by electroporation" *Proc. Natl. Acad. Sci. USA*, 82:5824 (1985).
Fromm, et al., "An octopine synthase enhancer element directs tissue-specific expression and binds ASF-1, a factor from tobacco nuclear extracts" *The Plant Cell*, 1:977-984 (1989).
Gardiner et al., "Development of a core FRLP map in maize using an immortalized $F_2$ population" *Genetics*, 134:917 (1993).
Gene References into Function (GeneRIF). Retrieved from the Internet: URL: http://www.ncbi.nlm.nih.gov/entrez/query.fcgi?db-gene&cmd=Retrieve&dopt=Graphics&1, document printed Jun. 6, 2005.
Ghosh et al. "Transgenic indica rice (*Oryza sativa* L.) plants obtained by direct gene transfer to protoplasts" *J. Biotechnol.*, 32:1-10 (1994).
Gleave, "A versatile binary vector system with a T-DNA organizational structure conducive to efficient integration of cloned DNA into the plant genome" *Plant Mol. Biol.*, 20:1203 (1992).
Golovkin et al., "An SC35-like protein and a novel serine/arginine-rich protein interact with *Arabidopsis* U1-70K protein" *J. Biol. Chem.* 274:36428 (1999).
Gould et al., "Transformation of *Zea mays* L. Using *Agrobacterium tummefaciens* and the shoot apex" *Plant Physiology*, 95:426 (1991).
Graves and Goldman, "The transformation of *Zea mays* seedling with *Agrobacterium tumefaciens*" *Plant Mol. Biol.*, 7:34 (1986).
Hamilton, "A binary-BAC system for plant transformation with high-molecular-weight DNA" *Gene*, 200:107-116 (1997).

Hamilton et al., "Antisense gene that inhibits synthesis of the hormone ethylene in transgenic plants" *Nature*, 346:284-287 (1990).

Hamilton et al., "Stable transfer of intact high molecular weight DNA into plant chromosomes" *Proc. Natl. Acad. Sci. USA*, 93:9975-9979 (1996).

Herrera-Estrella et al., "Chimeric genes as dominant selectable markers in plant cells" *EMBO J.*, 2:987 (1983).

Hong, et al., "Promoter sequences from two different *Brassica napus* tapetal oleosin-like genes direct tapetal expression of β-glucuronidase in transgenic *Brassica* plants" *Plant Molecular Biology*, 34(3), pp. 549-555 (1997).

Hosoyama et al. "Oryzacystatin exogenously introduced into protoplasts and regeneration of transgenic rice" *Biosci. Biotechnol. Biochem.*, 58:1500 (1994).

Hu et al., "*Escherichia coli* one- and two-hybrid systems for the analysis and identification of protein-protein interactions" *Methods*, 20:80 (2000).

Huynh et al., In: Glover NM (ed) DNA Cloning: A practical Approach, vol. 1 *Oxford: IRL Press* (1985).

Hyrup, et al., "Peptide Nucleic Acids (PNA): Synthesis, Properties and Potential Applications" *Bioorganic & Medicinal Chemistry*, 4(1), pp. 5-23 (1996).

Ichimura et al., "Isolation of ATMEKK1 (a MAP Kinase Kinase Kinase)- interacting proteins and analysis of a MAP Kinase cascade in *Arabidopsis*" *Biochem. Biophys. Res. Comm.* 253:532 (1998).

International Search Report from International Application No. PCT/US05/32680.

Ishida, et al., "High efficiency transformation of maize (*Zea mays* L.) mediated by *Agrobacterium tumefaciens*" *Nature Biotechnology*, vol. 14, pp. 745-750 (1996).

Keegstra and Cline, "Protein import and routing systems of chloroplasts" *The Plant Cell*, 11:557-570 (1999).

Keller and Manak (DNA Probes, 2nd Ed. pp. 1-25, c. 1993 by *Stockton Press*, New York, NY).

Klee et al. "Agrobacterium-mediated plant transformation and its further applications to plant biology" *Ann. Rev. of Plant Phys.*, 38:467 (1987).

Klein et al. "High-velocity microprojectiles for delivering nucleic acids into living cells" *Nature*, 327:773 (1987).

Kohler and Milstein "Continuous cultures of fused cells secreting antibody of predefined specificity" *Nature*, 256: 495 (1975).

Komari et al., "Vectors carrying two separate T-DNAs for co-transformation of higher plants mediated by *Agrobacterium tumefaciens* and segregation of transformants free from selection markers" *Plant J.*, 10:165 (1996).

Lam, et al., "Site-specific mutations alter in vitro factor binding and change promoter expression pattern in transgenic plants" *Pro. Natl. Acad. Sci. USA*, vol. 86, pp. 7890-7894 (1989).

Liljegren, "Interactions among Apetalai, Leafy, and Terminal Flower1 specify meristem fate" *Plant Cell*, 11:1007 (1999).

Luan, et al., "A rice cab gene promoter contains separate cis-Acting elements that regulate expression in dicot and monocot plants" *The Plant Cell*, 4:971-981 (1992).

Lubberstedt, et al., "Promoters from genes for plastid proteins possess regions with different sensitivities toward red and blue light" *Plant Physiol.*, 104:997-1006 (1994).

Luo et al., "Mapping sequence specific DNA-protein interactions: A versatile, quantitative method and its application to transcription factor XF1" *J. Mol. Biol.* 266:479 (1997).

Mariani et al., "A chimaeric ribonuclease-inhibitor gene restores fertility to male sterile plants" *Nature*, 357: 384-387 (1992).

Marra et al., "High throughput fingerprint analysis of large-insert clones" *Genomic Research*, 7:1072-1084 (1997).

Martinez et al., "Creation of ecdysone receptor chimeras in plants for controlled regulation of gene expression" *Mol. Gen. Genet.*, 261:546 (1999).

Marty, "Plant Vacuoles" *The Plant Cell*, 11:587-599 (1999).

Matsui, et al., NimbleGen 60mer *Arabidopsis* array; National Institute of Advanced Industrial Science and Technology (AIST); Jul. 7, 2004. Retrieved from the Internet: URL:http://www.ncbi.nlm.nih.gov/projects/geo/query/acc.cgi?acc=GPL1323.

Matsuoka, et al., "Tissue-specific light-regulated expression directed by the promoter of a C4 gene, maize pyruvate,orthophosphate dikinase, in a C3 plant, rice" *Proc. Natl. Acad. Sci. USA*, vol. 90, pp. 9586-9590 (1993).

Matteucci et al. "Synthesis of Deoxyoligonucleotides on a polymer support" *J. Am. Chem. Soc.*, 103:3185 (1981).

May, et al., "Generation of Transgenic Banana (*Musa acuminate*) Plants via *Agrobacterium*-Mediated Transformation" *Bio/Technology*, vol. 13, pp. 486-492 (1995).

McAlister-Henn et al., "Application of the yeast two-hybrid system" *Methods*, 19:330 (1999).

McCormac et al., "A flexible series of binary vectors for agrobacterium-mediated plant transformation" *Mol. Biotechnol.*, 8:199 (1997).

Michaels et al., "Flowering Locus C encodes a novel MADS domain protein that acts as a repressor of flowering" *The Plant Cell*, 11:949 (1999).

Mizutani, et al., "Cytochrome p450 superfamily in *Arabidopsis thaliana*: isolation of cDNAs, Differential Expression, and RFLP mapping of multiple cytochromes P450" *Plant Molecular Biology* 37, pp. 39-52 (1998).

Müller et al., "High meiotic stability of a foreign gene introduced into tobacco by *Agrobacterium*-mediated transformation" *Mol. Gen. Genet.*, 207:171 (1987).

Napoli et al., "Introduction of a chimeric chalcone synthase gene into petunia results in reversible co-suppression of homologous genes in trans." *The Plant Cell*, 2:279 (1990).

Needleman and Wunsch "A general method applicable to the search for similarities in the amino acid sequence of two proteins" *J. Mol. Biol.*, 48:443 (1970).

NSF 2010: Functional Genomics *Arabidopsis* P450s; Retrieved from the Internet: URL: http://arabidopsis-p450.biotec.uiuc.edu/, document undated.

Oeller et al., "Reversible inhibition of tomato fruit senescence by antisense RNA" *Science*, 254:437-439 (1991).

Pan, et al., "GAL4 transcription factor is not a "zinc finger" but forms a Zn(II)2Cys6 binuclear cluster" *Proc. Natl. Acad. Sci. USA*, vol. 87, pp. 2077-2081 (1990).

Panaud et al., "Frequency of microsatellite sequences in rice (*Oryza sative* L.)" *Genome*, 38:1170 (1995).

Paquette, et al., "Intron-Exon Organization and Phylogeny in a Large Superfamily, the Paralogous Cytochrome P450 Genes of *Arabidopsis thaliana*" *DNA and Cell Biology*, vol. 19, No. 5, pp. 307-317 (2000).

Paszkowski et al. "Direct gene transfer to plants" *EMBO J.*, 3:2717 (1984).

Pearson and Lipman "Improved tools for biological sequence comparison" *Proc. Natl. Acad. Sci. USA*, 85: 2444 (1988).

Perriman, et al., "Effective ribozyme delivery in plant cells" *Proc. Natl. Acad. Sci. USA*, vol. 92(13), pp. 6175-6179 (1995).

Refseth et al., "Hybridization capture of microsatellites directly from genomic DNA" *Electrophoresis*, 18:1519 (1997).

Riggs, et al., "Cotyledon Nuclear Proteins Bind to DNA Fragments Harboring Regulatory Elements of Phytohemagglutinin Genes" *The Plant Cell*, vol. 1(6), pp. 609-621 (1989).

Rivera, et al., "Genomic evidence for two functionality distinct gene classes" *Proc. Natl. Acad. Sci. USA*, vol. 95, pp. 6239-6244 (1998).

Salomon et al., "Genetic identification of functions of TR-DNA transcripts in octopine crown galls" *EMBO J.*, 3:141 (1984).

Sambrook et al. (Molecular Cloning, a Laboratory Manual, 2nd ed., c. 1989 by *Cold Spring Harbor Laboratory Press*, Cold Spring Harbor, NY).

Sato, et al., "Structural analysis of *Arabidopsis thaliana* chromosome 3. I. Sequence features of the regions of 4,504,864 bp covered by sixty P1 and TAC clones" *DNA Res.* 7 (2), 131-135 (2000).

Schwarz et al., "The basic region of myogenin cooperates with two transcription activation domains to induce muscle-specific transcription" *Mol. Cell. Biol.*, 12:266 (1992).

Senior et al., "Simple sequence repeat markers developed from Maize sequences found in the Genbank database: Map construction" *Crop Science*, 36:1676 (1996).

Sheehy et al., "Reduction of polygalacturonase activity in tomato fruit by antisense RNA" Proc. *Nat. Acad. Sci. USA*, 85:8805 (1988).

Shizuya et al., "Cloning and stable maintenance of 300-kilobase-pair fragments of human DNA in *Escherichia coli* using an F-factor-based vector" *Proc. Natl. Acad. Sci. USA*, 89:8794-8797 (1992).

Slocombe, et al., "Temporal and tissue-specific regulation of a *Brassica napus* stearoyl-acyl carrier protein desaturase gene" *Plant Physiol.*, 104(4):167-176 (1994).

Smith and Waterman, "Comparison of Biosequences" *Advances in Applied Mathematics.*, 2:482 (1981).

Sonnhammer, et al., "Pfam: multiple sequence alignments and HMM-profiles of protein domains" *Nucleic Acids Research*, vol. 26, (1998), pp. 320-322.

Sonnhammer, et al., "Pfam: A Comprehensive Database of Protein Domain Families Based on Seed Alignments", *Proteins: Structure, Function, and Genetics*, vol. 28 (1997), pp. 405-420.

Sternberg et al., "Bacteriophage P1 cloning system for the isolation, amplification, and recovery of DNA fragments as large as 100 kilobase pairs" *Proc. Natl. Acad. Sci. USA*, 87(1):103-7 (1990).

Summerton and Weller, Morpholino Antisense Oligomers: Design, Preparation, and Properties, *Antisense & Nucleic Acid Drug Development.*, 7, pp. 187-195 (1997).

Tanksley and McCouch, "Seed banks and molecular maps: Unlocking genetic potential from the wild" *Science*, 277:1063 (1997).

Taramino et al., "Simple sequence repeats for germplasm analysis and mapping in maize" *Genome*, 39:277 (1996).

Tian, et al., "How Well is Enzyme Function Conserved as a Function of Pairwise Sequence Identity?" *J. Mol. Biol.*, 333, pp. 863-882 (2003).

Tijessen, "Hybridization with Nucleic Acid Probes" in Laboratory Techniques in Biochemistry and Molecular Biology, P.C. vand der Vliet, ed., c. 1993 by *Elsevier*, Amsterdam.

Truernit, et al., "The promoter of the *Arabidopsis thaliana* SUC2 sucrose-H+ symporter gene directs expression of β-glucuronidase to the phloem: Evidence for phloem loading and unloading by SUC2" *Planta*, 196, pp. 564-570 (1995).

Urdea et al. "Chemical synthesis of a gene for human epidermal growth factor urogastrone and its expression in yeast" *Proc. Natl. Acad. Sci. USA*, 80:7461 (1983).

van der Krol et al., "Flavonoid genes in petunia: Addition of a limited number of gene copies my lead to a suppression of gene expression" *The Plant Cell*, 2:291 (1990).

Van Eenennaam, et al., "Elevation of seed χ-tocopherol levels using plant-based transcription factors targeted to an endogenous locus" *Metabolic Engineering*, 6, pp. 101-108 (2004).

Vaucheret et al., "Transgene-induced gene silencing in plants" *The Plant Journal*, 16:651-659 (1998).

Venkateswarlu et al., "Evidence for T-DNA mediated gene targeting to tobacco chloroplasts" *Biotechnology*, 9:1103 (1991).

Vergunst et al., "Site-specific integration of *Agrobacterium* T-DNA in *Arabidopsis thaliana* mediated by Cre recombinase" *Nucleic Acids Res.*, 26:2729 (1998).

Vergunst et al., "Cre/lox-mediated site-specific integration of *Agrobacterium* T-DNA in *Arabidopsis thaliana* by transient expression of cre" *Plant Mol. Biol.*, 38:393 (1998).

Vitale and Denecke, "The endoplasmic reticulum-gateway of the secretory pathway" *The Plant Cell*, 11:615-628 (1999).

Walden et al., "A novel 205-kilodalton testis-specific serine/threonine protein kinase associated with microtubules of the spermatid manchette" *Mol. Cell. Biol.*, 1:175-194 (1990).

Weising et al., "Foreign genes in plants: transfer, structure, expression, and applications" *Ann. Rev. Genet.*, 22:421 (1988).

Werck-Reichhart, et al., "Cytochromes P450; The *Arabidopsis* Book" (2002). Retrieved from the Internet: URL:http://www.arabidopsis.org/servlets/TairObject?type=publication&id=501681274.

Wilson, et al., "Assessing Annotation Transfer for Genomics: Quantifying the Relations between Protein Sequence, Structure and Function through Traditional and Probabilistic Scores" *J. Mol. Biol.* 297, pp. 233-249, (2000).

Xu, et al., "Microarray-based analysis of gene expression in very large gene families: the cytochrome P450 gene superfamily of *Arabidopsis thaliana*" *Gene*, 272, pp. 61-74 (2001).

Yamamoto, et al., "The Promoter of a Pine Photosynthetic Gene Allows Expression of a β-Glucuronidase Reporter Gene in Transgenic Rice Plants in a Light-Independent but Tissue Specific Manner" *Plant Cell Physiol.*, 35(5), pp. 773-778 (1994).

Yanagisawa, S., "The Dof family of plant transcription factors" *Trends in Plant Science*, vol. 7, No. 12; pp. 555-560 (2002).

Yanagisawa, et al., "Metabolic engineering with Dof1 transcription factor in plants: Improved nitrogen assimilation and growth under low-nitrogen conditions" *PNAS*, vol. 101, No. 20, pp. 7833-7838 (2004).

Zhang, et al., "Synthetic Zinc Finger Transcription Factor Action at an Endogenous Chromosomal Site" *The Journal of Biological Chemistry*, vol. 275, No. 43, pp. 33850-33860 (2000).

Zheng, et al., "SPK1 is an essential S-phase-specific gene of *Saccharomyces cerevisiae* that encodes a nuclear serine/threonine/tyrosine kinase" *Mol. Cell Biol.*, 13-5829-5842 (1993).

Notice of Allowance from U.S. Appl. No. 11/180,101, dated Apr. 28, 2008, 7 pages.

Notice of Allowance from U.S. Appl. No. 11/180,418, dated Mar. 28, 2008, 4 pages.

Response to Final Office Action from U.S. Appl. No. 11/357,357, filed Apr. 29, 2008, 5 pages; and Advisory Action, dated May 14, 2008, 3 pages.

Notice of Allowance from U.S. Appl. No. 11/362,437, dated Apr. 28, 2008, 7 pages.

Office Action from U.S. Appl. No. 11/368,323, dated Mar. 24, 2008, 8 pages.

Office Action from U.S. Appl. No. 11/388,215, dated Apr. 3, 2008, 7 pages.

Final Office Action from U.S. Appl. No. 11/369,168, dated Apr. 16, 2008, 9 pages.

Final Office Action from U.S. Appl. No. 11/370,253, dated May 16, 2008, 9 pages.

Final Office Action from U.S. Appl. No. 11/371,356, dated Apr. 17, 2008, 9 pages.

Final Office Action from U.S. Appl. No. 11/371,624, dated Apr. 16, 2008, 9 pages.

Notice of Allowance from U.S. Appl. No. 11/371,623, dated May 29, 2008, 8 pages.

Office Action from U.S. Appl. No. 11/387,751, dated May 23, 2008, 10 pages.

Response to Office Action from U.S. Appl. No. 11/388,215, filed Jul. 3, 2008, 5 pages.

Examiner Interview Summary from U.S. Appl. No. 11/370,253, dated Aug. 12, 2008, 2 pages; and Response to Final Office Action filed Aug. 18, 2008, 13 pages.

Response to Final Office Action from U.S. Appl. No. 11/371,356, filed Jun. 17, 2008, 4 pages; and Advisory Action, dated Aug. 6, 2008, 3 pages.

Response to Final Office Action from U.S. Appl. No. 11/371,624, filed Jun. 16, 2008, 5 pages; Advisory Action, dated Jul. 11, 2008, 4 pages; Examiner Interview Summary, dated Aug. 12, 2008, 2 page; and Response to Final Office Action filed Aug. 18, 2008, 13 pages.

Response to Office Action from U.S. App. No. 11/388,215, filed Jul. 3, 2008, 5 pages.

Office Action from U.S. Appl. No. 11/371,334, dated Jan. 8, 2009, 8 pages.

Office Action from U.S. Appl. No. 11/761,165, dated Feb. 4, 2009, 6 pages.

Office Action from U.S. Appl. No. 12/045,487, dated Mar. 31, 2009, 10 pages.

Examiner Interview Summary from U.S. Appl. No. 11/370,253, dated Aug. 12, 2008, 2 pages; and Response to Final Office Action filed Aug. 18, 2008, 13 pages; Response to Final Office Action filed Sep. 16, 2008, 20 pages; Advisory Action, dated Sep. 24, 2008, 3 pages; Notice of Appeal, filed Nov. 17, 2008, 1 page; and Notice of Allowance dated Apr. 17, 2009, 6 pages.

Response to Final Office Action from U.S. Appl. No. 11/371,356, filed Jun. 17, 2008, 4 pages; and Advisory Action, dated Aug. 6, 2008, 3 pages; Response to Final Office Action filed Sep. 16, 2008, 20 pages; Notice of Appeal, filed Oct. 16, 2008, 1 page; Advisory Action, dated Oct. 28, 2008, 3 pages; and Notice of Allowance dated Apr. 14, 2009, 6 pages.

Response to Final Office Action from U.S. App. No. 11/371,624, filed Jun. 16, 2008, 5 pages; Advisory Action, dated Jul. 11, 2008, 4 pages;

Examiner Interview Summary, dated Aug. 12, 2008, 2 pages; and Response to Final Office Action filed Aug. 18, 2008, 11 pages; Response to Final Office Action filed Sep. 16, 2008, 20 pages; Advisory Action dated Sep. 24, 2008, 3 pages; Notice of Appeal filed Oct. 16, 2008, 1 page; and Notice of Allowance dated Apr. 8, 2009, 6 pages.

Office Action from U.S. Appl. No. 12/040,538, dated Jun. 19, 2009, 18 pages; and Response to Office Action filed Aug. 5, 2009, 5 pages.

Notice of Allowance from U.S. Appl. No. 12/040,538, dated Sep. 22, 2009, 4 pages.

Office Action from U.S. Appl. No. 11/370,216, dated Sep. 30, 2009, 12 pages.

Office Action from U.S. Appl. No. 11/371,200, dated Sep. 17, 2009, 10 pages.

Office action from U.S. Appl. No. 11/371,632, dated Oct. 16, 2009, 8 pages.

* cited by examiner

US 7,691,991 B2

SEQUENCE-DETERMINED DNA FRAGMENTS ENCODING CYTOCHROME P450 PROTEINS

RELATED-APPLICATIONS

This application is a continuation-in-part of U.S. patent application Ser. No. 11/006,231 filed Dec. 6, 2004, which is a continuation of U.S. patent application Ser. No. 10/645,822 filed Aug. 22, 2003, which is a continuation-in-part of U.S. patent application Ser. No. 10/216,621 filed on Aug. 12, 2002, now abandoned which is a continuation of U.S. patent application Ser. No. 09/940,257 filed Aug. 24, 2001, now abandoned which is a continuation-in-part of U.S. patent application Ser. No. 09/832,192 filed on Apr. 11, 2001, now abandoned which claims the benefit of priority to U.S. Provisional Patent Application No. 60/197,870, filed Apr. 17, 2000. This application also is a continuation-in-part of U.S. patent application Ser. No. 11/006,231 filed Dec. 6, 2004, which is a continuation of U.S. patent application Ser. No. 10/645,822 filed Aug. 22, 2003, which is a continuation-in-part of U.S. patent application Ser. No. 10/461,476 filed on Jun. 16, 2003, now abandoned which is a continuation of U.S. patent application Ser. No. 10/191,406 filed Jul. 10, 2002, now abandoned which is a continuation of U.S. patent application Ser. No. 09/940,255 filed Aug. 24, 2001, which is a continuation-in-part of U.S. patent application Ser. No. 09/832,192, filed Apr. 11, 2001, which claims the benefit of priority to U.S. Provisional Patent Application No. 60/197,870, filed Apr. 17, 2000. This application also is a continuation-in-part of U.S. patent application Ser. No. 11/006,231 filed Dec. 6, 2004, which is a continuation of U.S. patent application Ser. No. 10/645,822 filed Aug. 22, 2003, which is a continuation-in-part of U.S. patent application Ser. No. 10/282,058 filed on Oct. 29, 2002, now abandoned which is a continuation-in-part of U.S. patent application Ser. No. 09/940,258 filed Aug. 24, 2001 now abandoned, and is a continuation-in-part of U.S. patent application Ser. No. 10/162,726, filed Jun. 6, 2002. U.S. patent application Ser. No. 09/940,258 filed Aug. 24, 2001, and U.S. patent application Ser. No. 10/162,726, filed Jun. 6, 2002, are continuation-in-part applications of U.S. patent application Ser. No. 09/832,192 filed on Apr. 11, 2001, which claims the benefit of priority to U.S. Provisional Patent Application No. 60/197,870, filed Apr. 17, 2000. The entire contents of these related applications are incorporated by reference in their entirety.

BACKGROUND

1. Technical Field

The present invention relates to isolated polynucleotides from plants that include a complete coding sequence, or a fragment thereof, that is expressed. In addition, the present invention relates to polypeptides or proteins encoded by the coding sequence of these polynucleotides. The present invention also relates to isolated polynucleotides that represent regulatory regions of genes. The present invention also relates to isolated polynucleotides that represent untranslated regions of genes. The present invention further relates to the use of these isolated polynucleotides and polypeptides and proteins.

2. Background Information

There are more than 300,000 species of plants. They show a wide diversity of forms, ranging from delicate liverworts, adapted for life in a damp habitat, to cacti, capable of surviving in the desert. The plant kingdom includes herbaceous plants, such as corn, whose life cycle is measured in months, to the giant redwood tree, which can live for thousands of years. This diversity reflects the adaptations of plants to survive in a wide range of habitats. This is seen most clearly in the flowering plants (phylum Angiospermophyta), which are the most numerous, with over 250,000 species. They are also the most widespread, being found from the tropics to the arctic.

When the molecular and genetic basis for different plant characteristics are understood, a wide variety of polynucleotides, both endogenous polynucleotides and created variants, polypeptides, cells, and whole organisms, can be exploited to engineer old and new plant traits in a vast range of organisms including plants. These traits can range from the observable morphological characteristics, through adaptation to specific environments to biochemical composition and to molecules that the plants (organisms) exude. Such engineering can involve tailoring existing traits, such as increasing the production of taxol in yew trees, to combining traits from two different plants into a single organism, such as inserting the drought tolerance of a cactus into a corn plant. Molecular and genetic knowledge also allows the creation of new traits. For example, the production of chemicals and pharmaceuticals that are not native to particular species or the plant kingdom as a whole.

SUMMARY

The present invention comprises polynucleotides, such as complete cDNA sequences and/or sequences of genomic DNA encompassing complete genes, fragments of genes, and/or regulatory elements of genes and/or regions with other functions and/or intergenic regions, hereinafter collectively referred to as Sequence-Determined DNA Fragments (SDFs) or sometimes collectively referred to as "genes or gene components", or sometimes as "genes, gene components or products", from different plant species, particularly corn, wheat, soybean, rice and *Arabidopsis thaliana*, and other plants and mutants, variants, fragments or fusions of said SDFs and polypeptides or proteins derived therefrom. In some instances, the SDFs span the entirety of a protein-coding segment. In some instances, the entirety of an mRNA is represented. Other objects of the invention that are also represented by SDFs of the invention are control sequences, such as, but not limited to, promoters. Complements of any sequence of the invention are also considered part of the invention.

Other objects of the invention are polynucleotides comprising exon sequences, polynucleotides comprising intron sequences, polynucleotides comprising introns together with exons, intron/exon junction sequences, 5' untranslated sequences, and 3' untranslated sequences of the SDFs of the present invention. Polynucleotides representing the joinder of any exons described herein, in any arrangement, for example, to produce a sequence encoding any desirable amino acid sequence are within the scope of the invention.

The present invention also resides in probes useful for isolating and identifying nucleic acids that hybridize to an SDF of the invention. The probes can be of any length, but typically are 12-2000 nucleotides in length; more typically, 15 to 200 nucleotides long; even more typically, 18 to 100 nucleotides long.

Yet another object of the invention is a method of isolating and/or identifying nucleic acids using the following steps: (a) contacting a probe of the instant invention with a polynucleotide sample under conditions that permit hybridization and formation of a polynucleotide duplex; and (b) detecting and/or isolating the duplex of step (a).

The conditions for hybridization can be from low to moderate to high stringency conditions. The sample can include a polynucleotide having a sequence unique in a plant genome. Probes and methods of the invention are useful, for example, without limitation, for mapping of genetic traits and/or for positional cloning of a desired fragment of genomic DNA.

Probes and methods of the invention can also be used for detecting alternatively spliced messages within a species. Probes and methods of the invention can further be used to detect or isolate related genes in other plant species using genomic DNA (gDNA) and/or cDNA libraries. In some instances, especially when longer probes and low to moderate stringency hybridization conditions are used, the probe will hybridize to a plurality of cDNA and/or gDNA sequences of a plant. This approach is useful for isolating representatives of gene families which are identifiable by possession of a common functional domain in the gene product or which have common cis-acting regulatory sequences. This approach is also useful for identifying orthologous genes from other organisms.

The present invention also resides in constructs for modulating the expression of the genes comprised of all or a fragment of an SDF. The constructs comprise all or a fragment of the expressed SDF, or of a complementary sequence. Examples of constructs include ribozymes comprising RNA encoded by an SDF or by a sequence complementary thereto, antisense constructs, constructs comprising coding regions or parts thereof, constructs comprising promoters, introns, untranslated regions, scaffold attachment regions, methylating regions, enhancing or reducing regions, DNA and chromatin conformation modifying sequences, etc. Such constructs can be constructed using viral, plasmid, bacterial artificial chromosomes (BACs), plasmid artificial chromosomes (PACs), autonomous plant plasmids, plant artificial chromosomes or other types of vectors and exist in the plant as autonomous replicating sequences or as DNA integrated into the genome. When inserted into a host cell, the construct is, preferably, functionally integrated with, or operatively linked to, a heterologous polynucleotide. For instance, a coding region from an SDF might be operably linked to a promoter that is functional in a plant.

The present invention also resides in host cells, including bacterial or yeast cells or plant cells, and plants that harbor constructs such as described above. Another aspect of the invention relates to methods for modulating expression of specific genes in plants by expression of the coding sequence of the constructs, by regulation of expression of one or more endogenous genes in a plant or by suppression of expression of the polynucleotides of the invention in a plant. Methods of modulation of gene expression include, without limitation, (1) inserting into a host cell additional copies of a polynucleotide comprising a coding sequence; (2) modulating an endogenous promoter in a host cell; (3) inserting antisense or ribozyme constructs into a host cell; and (4) inserting into a host cell a polynucleotide comprising a sequence encoding a variant, fragment, or fusion of the native polypeptides of the instant invention.

BRIEF DESCRIPTION OF THE TABLES

The SDFs of the instant invention are listed in Table 2; annotations relevant to the sequences shown in Table 2 are presented in Table 1. Each sequence corresponds to a clone number. Each clone number corresponds to at least one sequence in Table 2. Nucleotide sequences in Table 2 are "Maximum Length Sequences" (MLS) that are the sequence of an insert in a single clone.

Table 1 is a Reference Table which correlates each of the sequences and SEQ ID NOs in Table 2 with a corresponding Ceres clone number, Ceres sequence identifier, and other information about the individual sequence. Table 2 is a Sequence Table with the sequence of each nucleic acid and amino acid sequence.

In Table 1, each section begins with a line that identifies the corresponding internal Ceres clone by its ID number. Subsection (A) then provides information about the nucleotide sequence including the corresponding sequence in Table 2, and the internal Ceres sequence identifier ("Ceres seq_id"). Subsection (B) provides similar information about a polypeptide sequence, but additionally identifies the location of the start codon in the nucleotide sequence which codes for the polypeptide. Subsection (C) provides information (where present) regarding identified domains within the polypeptide and (where present) a name for the polypeptide. Finally, subsection (D) provides (where present) information concerning amino acids which are found to be related and have some sequence identity to the polypeptide sequences of Table 2. Those "related" sequences identified by a "gi" number are in the GenBank data base.

In Table 2, Xaa within an amino acid sequence denotes an ambiguous amino acid. An Xaa at the end of an amino acid sequence indicates a stop codon.

TABLE 1

Reference table.

(Ac) cDNA SEQ
    Pat. Appln. SEQ ID NO: 1 (SEQ ID NO: 9550 in U.S. Provisional Patent Application No. 60/197,870)
        Ceres SEQ ID NO: 2158130
      PolyP SEQ
        Pat. Appln. SEQ ID NO: 2 (SEQ ID NO: 9551 in U.S. Provisional Patent Application No. 60/197,870)
            Ceres SEQ ID NO 2158131
            Loc. SEQ ID NO 1: @ 1 nt.
            Loc. Sig. P. SEQ ID NO 2: @ 26 aa.
        (C) Pred. PP Nom. & Annot.
            Cytochrome P450
            Loc. SEQ ID NO 2: 29 -> 495 aa.
        (Dp) Rel. AA SEQ
            Align. NO 3925
            gi No 5915828
            Desp.: CYTOCHROME P450 71B5 >gi|3164132|dbj|BAA28533| (D78601) cytochrome P450 monooxygenase [*Arabidopsis thaliana*]

TABLE 1-continued

Reference table.

>gi|6630748|emb|CAB64231.1| (AL132958) CYTOCHROME P450 71B5 [*Arabidopsis thaliana*]
  % Idnt.: 75.4
  Align. Len.: 502
  Loc. SEQ ID NO 2: 1 -> 500 aa.
 PolyP SEQ
  Pat. Appln. SEQ ID NO: 3 (SEQ ID NO: 9552 in U.S. Provisional Patent Application No. 60/197,870)
  Ceres SEQ ID NO 2158132
  Loc. SEQ ID NO 1: @ 187 nt.
  Loc. Sig. P. SEQ ID NO 3: @ 18 aa.
  (C) Pred. PP Nom. & Annot.
   Cytochrome P450
   Loc. SEQ ID NO 3: 1 -> 433 aa.
  (Dp) Rel. AA SEQ
   Align. NO 3926
   gi No 5915828
   Desp.: CYTOCHROME P450 71B5 >gi|3164132|dbj|BAA28533| (D78601) cytochrome P450 monooxygenase [*Arabidopsis thaliana*]
>gi|6630748|emb|CAB64231.1| (AL132958) CYTOCHROME P450 71B5 [*Arabidopsis thaliana*]
  % Idnt.: 75.4
  Align. Len.: 502
  Loc. SEQ ID NO 3: 1 -> 438 aa.
 PolyP SEQ
  Pat. Appln. SEQ ID NO: 4 (SEQ ID NO: 9553 in U.S. Provisional Patent Application No. 60/197,870)
  Ceres SEQ ID NO 2158133
  Loc. SEQ ID NO 1: @ 367 nt.
  (C) Pred. PP Nom. & Annot.
   Cytochrome P450
   Loc. SEQ ID NO 4: 1 -> 373 aa.
  (Dp) Rel. AA SEQ
   Align. NO 3927
   gi No 5915828
   Desp.: CYTOCHROME P450 71B5 >gi|3164132|dbj|BAA28533| (D78601) cytochrome P450 monooxygenase [*Arabidopsis thaliana*]
>gi|6630748|emb|CAB64231.1| (AL132958) CYTOCHROME P450 71B5 [*Arabidopsis thaliana*]
  % Idnt.: 75.4
  Align. Len.: 502
  Loc. SEQ ID NO 4: 1 -> 378 aa.

TABLE 2

Sequence listing.

```
<210> 1
<211> 1503
<212> DNA (genomic)
<213> Arabidopsis thaliana
<220>
<221> —
<222> 1 . . . 1503
<223> Ceres Seq. ID no. 2158130
<400> 1
atgtcgatct ctctctattt cctttgctc ttgcctctct ttttaatctt cttcaaaaag    60
ctctcacctt ctaaaggaaa gcttcctcct ggacctctag gtcttccgat tatcgggaac   120
ttgcaccaac ttggaaaatc tctccataga tcttttcata aactttctca aaactatgga   180
cccgtgatgt ttctacattt cggtgtggtc cctgtggttg tggtctccac aagagaagca   240
gctgaagaag ttctcaagac tcatgatctc gagacttgta cccgaccaaa gctaacagcg   300
accaaattgt tttcttacaa ctacaaagac attggcttcg ctcaatacgg tgatgactgg   360
agagagatga ggaagcttgc gatgctcgag cttttttagct cgaaaaagct caaggctttc   420
aggtatatta gaagaagaga gagtgaagtc ctagtcaata aactctcgaa atctgctgag   480
acacgaacta tggtagactt gagaaaagct ctttttctctt ataccgctag tatcgtatgt   540
```

TABLE 2-continued

Sequence listing.

```
agactcgctt ttggacagaa cttccatgag tgcgattttg tcgatatgga taaagttgaa   600
gatcttgtgc tcgaatctga gaccaatctt ggctcattcg cgttcactga cttcttcccc   660
gcaggtcttg ggtgggttat agaccggatc tctggccaac attcggagtt gcacaaagcc   720
tttgctagac ttagtaattt ctttcaacat gtgatcgatg atcacttgaa gcccgggcaa   780
tctcaagatc attcagacat cattggtgtc atgttagata tgatcaataa agagagtaaa   840
gtcggttcct tccaagtcac ctacgaccat cttaaaggag tcatgtcgga tgtgttttta   900
gcgggagtga acgcaggagc gatcacaatg atatgggcga tgacagagct agccagacat   960
ccgagagtga tgaagaaact tcaacaagag attcgagaaa tactcggaga caacaaagaa  1020
aaaatcacgg aacaagatct cgaaaaggtt cactacttga aacttgtgat cgaagaaaca  1080
ttcagattac atcctccagc tcctctcttg ctacctagag agacaatgtc tgacttaaag  1140
attcaaggct acaatattcc caagaacacg atgatagaga tcaatactta ttcaatagga  1200
cgcgatccta attgctggga aaaccctaac gatttcaacc cggagagatt tatcgatagc  1260
cctgtcgaat ataagggtca acattacgag ttgttgcctt ttggtgctgg tcgcaggatt  1320
tgtccaggaa tggctacggg gataactatc gtcgagctcg gtttacttaa tgttctttac  1380
ttctttgatt ggagtttgcc tgatggaatg aaaattgaag acatagacat ggaagaagct  1440
ggagctttcg tcgtcgccaa gaaagtccct cttgagctga ttccaactcc acatcagtgg  1500
tga                                                                1503
```

<210> 2
<211> 500
<213> *Arabidopsis thaliana*
<220>
<221> peptide
<222> 1 . . . 500
<223> Ceres Seq. ID no. 2158131
<400> 2

```
Met Ser Ile Ser Leu Tyr Phe Leu Leu Leu Pro Leu Phe Leu Ile
1               5                  10                  15

Phe Phe Lys Lys Leu Ser Pro Ser Lys Gly Lys Leu Pro Pro Gly Pro
            20                  25                  30

Leu Gly Leu Pro Ile Ile Gly Asn Leu His Gln Leu Gly Lys Ser Leu
        35                  40                  45

His Arg Ser Phe His Lys Leu Ser Gln Asn Tyr Gly Pro Val Met Phe
    50                  55                  60

Leu His Phe Gly Val Val Pro Val Val Val Ser Thr Arg Glu Ala
65                  70                  75                  80

Ala Glu Glu Val Leu Lys Thr His Asp Leu Glu Thr Cys Thr Arg Pro
                85                  90                  95

Lys Leu Thr Ala Thr Lys Leu Phe Ser Tyr Asn Tyr Lys Asp Ile Gly
            100                 105                 110

Phe Ala Gln Tyr Gly Asp Asp Trp Arg Glu Met Arg Lys Leu Ala Met
        115                 120                 125

Leu Glu Leu Phe Ser Ser Lys Lys Leu Lys Ala Phe Arg Tyr Ile Arg
    130                 135                 140

Glu Glu Glu Ser Glu Val Leu Val Asn Lys Leu Ser Lys Ser Ala Glu
145                 150                 155                 160

Thr Arg Thr Met Val Asp Leu Arg Lys Ala Leu Phe Ser Tyr Thr Ala
                165                 170                 175

Ser Ile Val Cys Arg Leu Ala Phe Gly Gln Asn Phe His Glu Cys Asp
            180                 185                 190
```

TABLE 2-continued

Sequence listing.

```
Phe Val Asp Met Asp Lys Val Glu Asp Leu Val Leu Glu Ser Glu Thr
            195                 200                 205

Asn Leu Gly Ser Phe Ala Phe Thr Asp Phe Pro Ala Gly Leu Gly
        210                 215                 220

Trp Val Ile Asp Arg Ile Ser Gly Gln His Ser Glu Leu His Lys Ala
225                 230                 235                 240

Phe Ala Arg Leu Ser Asn Phe Phe Gln His Val Ile Asp Asp His Leu
                245                 250                 255

Lys Pro Gly Gln Ser Gln Asp His Ser Asp Ile Ile Gly Val Met Leu
            260                 265                 270

Asp Met Ile Asn Lys Glu Ser Lys Val Gly Ser Phe Gln Val Thr Tyr
            275                 280                 285

Asp His Leu Lys Gly Val Met Ser Asp Val Phe Leu Ala Gly Val Asn
        290                 295                 300

Ala Gly Ala Ile Thr Met Ile Trp Ala Met Thr Glu Leu Ala Arg His
305                 310                 315                 320

Pro Arg Val Met Lys Lys Leu Gln Gln Glu Ile Arg Glu Ile Leu Gly
                325                 330                 335

Asp Asn Lys Glu Lys Ile Thr Glu Gln Asp Leu Glu Lys Val His Tyr
            340                 345                 350

Leu Lys Leu Val Ile Glu Glu Thr Phe Arg Leu His Pro Pro Ala Pro
        355                 360                 365

Leu Leu Leu Pro Arg Glu Thr Met Ser Asp Leu Lys Ile Gln Gly Tyr
    370                 375                 380

Asn Ile Pro Lys Asn Thr Met Ile Glu Ile Asn Thr Tyr Ser Ile Gly
385                 390                 395                 400

Arg Asp Pro Asn Cys Trp Glu Asn Pro Asn Asp Phe Asn Pro Glu Arg
                405                 410                 415

Phe Ile Asp Ser Pro Val Glu Tyr Lys Gly Gln His Tyr Glu Leu Leu
            420                 425                 430

Pro Phe Gly Ala Gly Arg Arg Ile Cys Pro Gly Met Ala Thr Gly Ile
        435                 440                 445

Thr Ile Val Glu Leu Gly Leu Leu Asn Val Leu Tyr Phe Phe Asp Trp
    450                 455                 460

Ser Leu Pro Asp Gly Met Lys Ile Glu Asp Ile Asp Met Glu Glu Ala
465                 470                 475                 480

Gly Ala Phe Val Val Ala Lys Lys Val Pro Leu Glu Leu Ile Pro Thr
                485                 490                 495

Pro His Gln Trp
            500

<210> 3
<211> 438
<213> Arabidopsis thaliana
<220>
<221> peptide
<222> 1 . . . 438
<223> Ceres Seq. ID no. 2158132
<400> 3
Met Phe Leu His Phe Gly Val Val Pro Val Val Val Ser Thr Arg
1               5                   10                  15

Glu Ala Ala Glu Glu Val Leu Lys Thr His Asp Leu Glu Thr Cys Thr
            20                  25                  30

Arg Pro Lys Leu Thr Ala Thr Lys Leu Phe Ser Tyr Asn Tyr Lys Asp
        35                  40                  45
```

TABLE 2-continued

Sequence listing.

```
Ile Gly Phe Ala Gln Tyr Gly Asp Asp Trp Arg Glu Met Arg Lys Leu
 50                  55                  60
Ala Met Leu Glu Leu Phe Ser Ser Lys Leu Lys Ala Phe Arg Tyr
 65                  70                  75                  80
Ile Arg Glu Glu Ser Glu Val Leu Val Asn Lys Leu Ser Lys Ser
                     85                  90                  95
Ala Glu Thr Arg Thr Met Val Asp Leu Arg Lys Ala Leu Phe Ser Tyr
                    100                 105                 110
Thr Ala Ser Ile Val Cys Arg Leu Ala Phe Gly Gln Asn Phe His Glu
                115                 120                 125
Cys Asp Phe Val Asp Met Asp Lys Val Glu Asp Leu Val Leu Glu Ser
130                 135                 140
Glu Thr Asn Leu Gly Ser Phe Ala Phe Thr Asp Phe Phe Pro Ala Gly
145                 150                 155                 160
Leu Gly Trp Val Ile Asp Arg Ile Ser Gly Gln His Ser Glu Leu His
                165                 170                 175
Lys Ala Phe Ala Arg Leu Ser Asn Phe Phe Gln His Val Ile Asp Asp
                180                 185                 190
His Leu Lys Pro Gly Gln Ser Gln Asp His Ser Asp Ile Ile Gly Val
                195                 200                 205
Met Leu Asp Met Ile Asn Lys Glu Ser Lys Val Gly Ser Phe Gln Val
                210                 215                 220
Thr Tyr Asp His Leu Lys Gly Val Met Ser Asp Val Phe Leu Ala Gly
225                 230                 235                 240
Val Asn Ala Gly Ala Ile Thr Met Ile Trp Ala Met Thr Glu Leu Ala
                245                 250                 255
Arg His Pro Arg Val Met Lys Lys Leu Gln Gln Glu Ile Arg Glu Ile
                260                 265                 270
Leu Gly Asp Asn Lys Glu Lys Ile Thr Glu Gln Asp Leu Glu Lys Val
                275                 280                 285
His Tyr Leu Lys Leu Val Ile Glu Glu Thr Phe Arg Leu His Pro Pro
                290                 295                 300
Ala Pro Leu Leu Leu Pro Arg Glu Thr Met Ser Asp Leu Lys Ile Gln
305                 310                 315                 320
Gly Tyr Asn Ile Pro Lys Asn Thr Met Ile Glu Ile Asn Thr Tyr Ser
                325                 330                 335
Ile Gly Arg Asp Pro Asn Cys Trp Glu Asn Pro Asn Asp Phe Asn Pro
                340                 345                 350
Glu Arg Phe Ile Asp Ser Pro Val Glu Tyr Lys Gly Gln His Tyr Glu
                355                 360                 365
Leu Leu Pro Phe Gly Ala Gly Arg Arg Ile Cys Pro Gly Met Ala Thr
370                 375                 380
Gly Ile Thr Ile Val Glu Leu Gly Leu Leu Asn Val Leu Tyr Phe Phe
385                 390                 395                 400
Asp Trp Ser Leu Pro Asp Gly Met Lys Ile Glu Ile Asp Met Glu
                405                 410                 415
Glu Ala Gly Ala Phe Val Val Ala Lys Lys Val Pro Leu Glu Leu Ile
                420                 425                 430
Pro Thr Pro His Gln Trp
                435
```

<210> 4

TABLE 2-continued

Sequence listing.

```
<211> 378
<213> Arabidopsis thaliana
<220>
<221> peptide
<222> 1 . . . 378
<223> Ceres Seq. ID no. 2158133
<400> 4
```

Met Arg Lys Leu Ala Met Leu Glu Leu Phe Ser Ser Lys Lys Leu Lys
1               5                   10                  15

Ala Phe Arg Tyr Ile Arg Glu Glu Ser Glu Val Leu Val Asn Lys
            20                  25                  30

Leu Ser Lys Ser Ala Glu Thr Arg Thr Met Val Asp Leu Arg Lys Ala
        35                  40                  45

Leu Phe Ser Tyr Thr Ala Ser Ile Val Cys Arg Leu Ala Phe Gly Gln
        50                  55                  60

Asn Phe His Glu Cys Asp Phe Val Asp Met Asp Lys Val Glu Asp Leu
65                  70                  75                  80

Val Leu Glu Ser Glu Thr Asn Leu Gly Ser Phe Ala Phe Thr Asp Phe
                85                  90                  95

Phe Pro Ala Gly Leu Gly Trp Val Ile Asp Arg Ile Ser Gly Gln His
            100                 105                 110

Ser Glu Leu His Lys Ala Phe Ala Arg Leu Ser Asn Phe Gln His
            115                 120                 125

Val Ile Asp Asp His Leu Lys Pro Gly Gln Ser Gln Asp His Ser Asp
130                 135                 140

Ile Ile Gly Val Met Leu Asp Met Ile Asn Lys Glu Ser Lys Val Gly
145                 150                 155                 160

Ser Phe Gln Val Thr Tyr Asp His Leu Lys Gly Val Met Ser Asp Val
                165                 170                 175

Phe Leu Ala Gly Val Asn Ala Gly Ala Ile Thr Met Ile Trp Ala Met
            180                 185                 190

Thr Glu Leu Ala Arg His Pro Arg Val Met Lys Lys Leu Gln Gln Glu
            195                 200                 205

Ile Arg Glu Ile Leu Gly Asp Asn Lys Glu Lys Ile Thr Glu Gln Asp
        210                 215                 220

Leu Glu Lys Val His Tyr Leu Lys Leu Val Ile Glu Glu Thr Phe Arg
225                 230                 235                 240

Leu His Pro Pro Ala Pro Leu Leu Leu Pro Arg Glu Thr Met Ser Asp
                245                 250                 255

Leu Lys Ile Gln Gly Tyr Asn Ile Pro Lys Asn Thr Met Ile Glu Ile
            260                 265                 270

Asn Thr Tyr Ser Ile Gly Arg Asp Pro Asn Cys Trp Glu Asn Pro Asn
            275                 280                 285

Asp Phe Asn Pro Glu Arg Phe Ile Asp Ser Pro Val Glu Tyr Lys Gly
        290                 295                 300

Gln His Tyr Glu Leu Leu Pro Phe Gly Ala Gly Arg Arg Ile Cys Pro
305                 310                 315                 320

Gly Met Ala Thr Gly Ile Thr Ile Val Glu Leu Gly Leu Leu Asn Val
                325                 330                 335

Leu Tyr Phe Phe Asp Trp Ser Leu Pro Asp Gly Met Lys Ile Glu Asp
            340                 345                 350

TABLE 2-continued

Sequence listing.

Ile Asp Met Glu Glu Ala Gly Ala Phe Val Val Ala Lys Lys Val Pro
        355                 360                 365

Leu Glu Leu Ile Pro Thr Pro His Gln Trp
    370                 375

DETAILED DESCRIPTION

The invention relates to polynucleotides and methods of use thereof, such as probes, primers and substrates; methods of detection and isolation; hybridization; methods of mapping; southern blotting; isolating cDNA from related organisms; isolating and/or identifying orthologous genes; methods of inhibiting gene expression (e.g., antisense, ribozyme constructs, chimeraplasts, co-suppression, transcriptional silencing, and other methods to inhibit gene expression); methods of functional analysis; promoter sequences and their use; utrs and/or intron sequences and their use; and coding sequences and their use.

The invention also relates to polypeptides and proteins and methods of use thereof, such as native polypeptides and proteins; antibodies; in vitro applications; polypeptide variants, fragments and fusions.

The invention also includes methods of modulating polypeptide production, such as suppression (e.g., antisense, ribozymes, co-suppression, insertion of sequences into the gene to be modulated, promoter modulation, expression of genes containing dominant-negative mutations) and enhanced expression (e.g., insertion of an exogenous gene and promoter modulation).

The invention further concerns gene constructs and vector construction, such as coding sequences, promoters, and signal peptides. the invention still further relates to transformation techniques.

Polynucleotides

Exemplified SDFs of the invention represent fragments of the genome of corn, wheat, rice, soybean or *Arabidopsis* and/or represent mRNA expressed from that genome. The isolated nucleic acid of the invention also encompasses corresponding fragments of the genome and/or cDNA complement of other organisms as described in detail below.

Polynucleotides of the invention can be isolated from polynucleotide libraries using primers comprising sequences similar to those described in the attached Table 2 or complements thereof. See, for example, the methods described in Sambrook et al. (Molecular Cloning, a Laboratory Manual, 2nd ed., c. 1989 by Cold Spring Harbor Laboratory Press, Cold Spring Harbor, N.Y.).

Alternatively, the polynucleotides of the invention can be produced by chemical synthesis. Such synthesis methods are described below.

It is contemplated that the nucleotide sequences presented herein may contain some small percentage of errors. These errors may arise in the normal course of determination of nucleotide sequences. Sequence errors can be corrected by obtaining seeds such as those deposited under the accession numbers cited herein, propagating them, isolating genomic DNA or appropriate mRNA from the resulting plants or seeds thereof, amplifying the relevant fragment of the genomic DNA or mRNA using primers having a sequence that flanks the erroneous sequence, and sequencing the amplification product.

Probes, Primers and Substrates

Probes and primers of the instant invention will hybridize to a polynucleotide comprising a sequence in Table 2. Though many different nucleotide sequences can encode an amino acid sequence, in some instances, the sequences of Table 2 are preferred for encoding polypeptides of the invention. However, the sequence of the probes and/or primers of the instant invention need not be identical to those in Table 2 or the complements thereof. Some variation in the sequence and length can lead to increase assay sensitivity if the nucleic acid probe can form a duplex with a target nucleotide in a sample that can be detected or isolated. The probes and/or primers of the invention can include additional nucleotides that may be helpful as a label to detect the formed duplex or for later cloning purposes.

Probe length will vary depending on the application. For use as a PCR primer, probes should be 12-40 nucleotides, preferably 18-30 nucleotides long. For use in mapping, probes should be 50 to 500 nucleotides, preferably 100-250 nucleotides long. For Southern hybridizations, probes as long as several kilobases can be used as explained below.

The probes and/or primers can be produced by synthetic procedures such as the triester method of Matteucci et al. (*J. Am. Chem. Soc.*, 103:3185 (1981)); or according to Urdea et al. (*Proc. Natl. Acad. Sci. USA*, 80:7461 (1981)) or using commercially available automated oligonucleotide synthesizers.

Methods of Detection and Isolation

The polynucleotides of the invention can be utilized in a number of methods known to those skilled in the art as probes and/or primers to isolate and detect polynucleotides, including, without limitation: Southern blot assays, Northern blot assays, Branched DNA hybridization assays, polymerase chain reaction, and microarray assays, and variations thereof. Specific methods given by way of examples, and discussed below include: hybridization, methods of mapping, Southern blotting, isolating cDNA from related organisms, and isolating and/or identifying orthologous genes.

Hybridization

The isolated SDFs of Tables 1 and 2 can be used as probes and/or primers for detection and/or isolation of related polynucleotide sequences through hybridization. Hybridization of one nucleic acid to another constitutes a physical property that defines the subject SDF of the invention and the identified related sequences. Also, such hybridization imposes structural limitations on the pair. A good general discussion of the factors for determining hybridization conditions is provided by Sambrook et al. (Molecular Cloning, a Laboratory Manual, 2nd ed., c. 1989 by Cold Spring Harbor Laboratory Press, Cold Spring Harbor, N.Y.; see esp., chapters 11 and 12). Additional considerations and details of the physical chemistry of hybridization are provided by Keller and Manak (DNA Probes, 2$^{nd}$ Ed. pp. 1-25, c. 1993 by Stockton Press, New York, N.Y.).

Depending on the stringency of the conditions under which these probes and/or primers are used, polynucleotides exhibiting a wide range of similarity to those in Tables 1 or 2 or fragments thereof can be detected or isolated. When the practitioner wishes to examine the result of membrane hybridizations under a variety of stringencies, an efficient way to do so is to perform the hybridization under a low stringency condition, then to wash the hybridization membrane under increasingly stringent conditions.

When using SDFs to identify orthologous genes in other species, the practitioner will preferably adjust the amount of target DNA of each species so that, as nearly as is practical, the same number of genome equivalents are present for each species examined. This prevents faint signals from species having large genomes, and thus small numbers of genome equivalents per mass of DNA, from erroneously being interpreted as absence of the corresponding gene in the genome.

The probes and/or primers of the instant invention can also be used to detect or isolate nucleotides that are "identical" to the probes or primers. Two nucleic acid sequences or polypeptides are said to be "identical" if the sequence of nucleotides or amino acid residues, respectively, in the two sequences is the same when aligned for maximum correspondence as described below.

Isolated polynucleotides within the scope of the invention also include allelic variants of the specific sequences presented in Tables 1 and 2. The probes and/or primers of the invention can also be used to detect and/or isolate polynucleotides exhibiting at least 80% sequence identity with the sequences of Table 1 or 2.

With respect to nucleotide sequences, degeneracy of the genetic code provides the possibility to substitute at least one base of the base sequence of a gene with a different base without causing the amino acid sequence of the polypeptide produced from the gene to be changed. Hence, the DNA of the present invention may also have any base sequence that has been changed from a sequence in Table 1 or 2 by substitution in accordance with degeneracy of genetic code. References describing codon usage include: Carels et al., (*J. Mol. Evol.*, 46:45 (1998)) and Fennoy et al. (*Nucl. Acids Res.*, 21(23): 5294 (1993)).

Mapping

The isolated SDFs provided herein can be used to create various types of genetic and physical maps of the genome of corn, *Arabidopsis*, soybean, rice, wheat, or other plants. Some SDFs may be absolutely associated with particular phenotypic traits, allowing construction of gross genetic maps. While not all SDFs of Table 2 of the priority patent applications will immediately be associated with a phenotype, all SDFs can be used as probes for identifying polymorphisms associated with phenotypes of interest. Briefly, one method of mapping involves total DNA isolation from individuals. It is subsequently cleaved with one or more restriction enzymes, separated according to mass, transferred to a solid support, hybridized with SDF DNA, and the pattern of fragments compared. Polymorphisms associated with a particular SDF are visualized as differences in the size of fragments produced between individual DNA samples after digestion with a particular restriction enzyme and hybridization with the SDF. After identification of polymorphic SDF sequences, linkage studies can be conducted. By using the individuals showing polymorphisms as parents in crossing programs, F2 progeny recombinants or recombinant inbreds, for example, are then analyzed. The order of DNA polymorphisms along the chromosomes can be determined based on the frequency with which they are inherited together versus independently. The closer two polymorphisms are together in a chromosome; the higher the probability that they are inherited together. Integration of the relative positions of all the polymorphisms and associated marker SDFs can produce a genetic map of the species, where the distances between markers reflect the recombination frequencies in that chromosome segment.

The use of recombinant inbred lines for such genetic mapping is described for *Arabidopsis* by Alonso-Blanco et al. (*Methods in Molecular Biology, vol.* 82, "*Arabidopsis Protocols*", pp. 137-146, J. M. Martinez-Zapater and J. Salinas, eds., c. 1998 by Humana Press, Totowa, N.J.) and for corn by Burr ("Mapping Genes with Recombinant Inbreds", pp. 249-254. In Freeling, M. and V. Walbot (Ed.), *The Maize Handbook*, c. 1994 by Springer-Verlag New York, Inc.: New York, N.Y., USA; Berlin Germany; Burr et al., *Genetics*, 118:519 (1998); and Gardiner et al., *Genetics*, 134:917 (1993)). This procedure, however, is not limited to plants and can be used for other organisms such as yeast or for individual cells.

The SDFs provided herein can also be used for simple sequence repeat (SSR) mapping. Rice SSR mapping is described elsewhere (Morgante et al., *The Plant Journal*, 3:165 (1993)), Panaud et al., *Genome*, 38:1170 (1995); Senior et al., *Crop Science*, 36:1676 (1996), Taramino et al., *Genome*, 39:277 (1996); and Ahn et al., *Molecular and General Genetics*, 241:483-90 (1993)). SSR mapping can be achieved using various methods. In one instance, polymorphisms are identified when sequence specific probes contained within an SDF flanking an SSR are made and used in polymerase chain reaction (PCR) assays with template DNA from two or more individuals of interest. Here, a change in the number of tandem repeats between the SSR-flanking sequences produces differently sized fragments (U.S. Pat. No. 5,766,847). Alternatively, polymorphisms can be identified by using the PCR fragment produced from the SSR-flanking sequence specific primer reaction as a probe against Southern blots representing different individuals (Refseth et al., *Electrophoresis*, 18:1519 (1997)).

Genetic and physical maps of crop species have many uses. For example, these maps can be used to devise positional cloning strategies for isolating novel genes from the mapped crop species. In addition, because the genomes of closely related species are largely syntenic (that is, they display the same ordering of genes within the genome), these maps can be used to isolate novel alleles from relatives of crop species by positional cloning strategies.

The various types of maps discussed above can be used with the SDFs provided herein to identify Quantitative Trait Loci (QTLs). Many important crop traits, such as the solids content of tomatoes, are quantitative traits and result from the combined interactions of several genes. These genes reside at different loci in the genome, oftentimes on different chromosomes, and generally exhibit multiple alleles at each locus. The SDFs provided herein can be used to identify QTLs and isolate specific alleles as described by de Vicente and Tanksley (*Genetics* 134:585 (1993)). In addition to isolating QTL alleles in present crop species, the SDFs provided herein can also be used to isolate alleles from the corresponding QTL of wild relatives. Transgenic plants having various combinations of QTL alleles can then be created, and the effects of the combinations measured. Once a desired allele combination has been identified, crop improvement can be accomplished either through biotechnological means or by directed conventional breeding programs (for review, see Tanksley and McCouch, *Science*, 277:1063 (1997)).

In another embodiment, the SDFs provided herein can be used to help create physical maps of the genome of corn, *Arabidopsis*, and related species. Where SDFs have been ordered on a genetic map, as described above, they can be used as probes to discover which clones in large libraries of plant DNA fragments in YACs, BACs, etc. contain the same SDF or similar sequences, thereby facilitating the assignment of the large DNA fragments to chromosomal positions. Subsequently, the large BACs, YACs, etc. can be ordered unambiguously by more detailed studies of their sequence composition (see, e.g., Marra et al., *Genomic Research*, 7:1072-1084 (1997)) and by using their end or other sequences to find the identical sequences in other cloned DNA fragments. The overlapping of DNA sequences in this way allows large contigs of plant sequences to be built that, when sufficiently extended, provide a complete physical map of a chromosome. Sometimes the SDFs themselves will provide the means of joining cloned sequences into a contig.

The patent publication WO95/35505 and U.S. Pat. Nos. 5,445,943 and 5,410,270 describe scanning multiple alleles of a plurality of loci using hybridization to arrays of oligonucleotides. These techniques are useful for each of the types of mapping discussed above.

Following the procedures described above and using a plurality of the SDFs of Table 2 or Table 2 on any of the priority patent applications, any individual can be genotyped. These individual genotypes can be used for the identification of particular cultivars, varieties, lines, ecotypes, and genetically modified plants or can serve as tools for subsequent genetic studies involving multiple phenotypic traits.

Southern Blot Hybridization

The sequences of Tables 1 and 2 can be used as probes for various hybridization techniques. These techniques are useful for detecting target polynucleotides in a sample or for determining whether transgenic plants, seeds or host cells harbor a gene or sequence of interest and thus might be expected to exhibit a particular trait or phenotype.

In addition, the SDFs provided herein can be used to isolate additional members of gene families from the same or different species and/or orthologous genes from the same or different species. This is accomplished by hybridizing an SDF to, for example, a Southern blot containing the appropriate genomic DNA or cDNA. Given the resulting hybridization data, one of ordinary skill in the art could distinguish and isolate the correct DNA fragments by size, restriction sites, sequence, and stated hybridization conditions from a gel or from a library.

Identification and isolation of orthologous genes from closely related species and alleles within a species is particularly desirable because of their potential for crop improvement. Many important crop traits, such as the solid content of tomatoes, result from the combined interactions of the products of several genes residing at different loci in the genome. Generally, alleles at each of these loci can make quantitative differences to the trait. By identifying and isolating numerous alleles for each locus from within or different species, transgenic plants with various combinations of alleles can be created, and the effects of the combinations measured. Once a more favorable allele combination has been identified, crop improvement can be accomplished either through biotechnological means or by directed conventional breeding programs (Tanksley et al., *Science*, 277:1063 (1997)).

The results from hybridizations of an SDFs provided herein to, for example, Southern blots containing DNA from another species can also be used to generate restriction fragment maps for the corresponding genomic regions. These maps provide additional information about the relative positions of restriction sites within fragments, further distinguishing mapped DNA from the remainder of the genome. Physical maps can be made by digesting genomic DNA with different combinations of restriction enzymes.

Probes for Southern blotting to distinguish individual restriction fragments can range in size from 15 to 20 nucleotides to several thousand nucleotides. More preferably, the probe is 100 to 1,000 nucleotides long for identifying members of a gene family when it is found that repetitive sequences would complicate the hybridization. For identifying an entire corresponding gene in another species, the probe is more preferably the length of the gene, typically 2,000 to 10,000 nucleotides, but probes 50-1,000 nucleotides long might be used. Some genes, however, might require probes up to 1,500 nucleotides long or overlapping probes constituting the full-length sequence to span their lengths.

Also, while it is preferred that the probe be homogeneous with respect to its sequence, it is not necessary. For example, as described below, a probe representing members of a gene family having diverse sequences can be generated using PCR to amplify genomic DNA or RNA templates using primers derived from SDFs that include sequences that define the gene family.

For identifying corresponding genes in another species, the next most preferable probe is a cDNA spanning the entire coding sequence, which allows all of the mRNA-coding fragment of the gene to be identified. Probes for Southern blotting can easily be generated from SDFs by making primers having the sequence at the ends of the SDF and using corn or *Arabidopsis* genomic DNA as a template. In instances where the SDF includes sequence conserved among species, primers including the conserved sequence can be used for PCR with genomic DNA from a species of interest to obtain a probe.

Similarly, if the SDF includes a domain of interest, that fragment of the SDF can be used to make primers and, with appropriate template DNA, used to make a probe to identify genes containing the domain. Alternatively, the PCR products can be resolved, for example by gel electrophoresis, and cloned and/or sequenced. Using Southern hybridization, the variants of the domain among members of a gene family, both within and across species, can be examined.

Isolating DNA from Related Organisms

The SDFs provided herein can be used to isolate the corresponding DNA from other organisms. Either cDNA or genomic DNA can be isolated. For isolating genomic DNA, a lambda, cosmid, BAC, or YAC, or other large insert genomic library from the plant of interest can be constructed using standard molecular biology techniques as described in detail by Sambrook et al. (Molecular Cloning: A Laboratory Manual, $2^{nd}$ ed. Cold Spring Harbor Laboratory Press, New York (1989)) and by Ausubel et al. (Current Protocols in Molecular Biology, Greene Publishing, New York (1992)).

To screen a phage library, for example, recombinant lambda clones are plated out on appropriate bacterial medium using an appropriate *E. coli* host strain. The resulting plaques are lifted from the plates using nylon or nitrocellulose filters. The plaque lifts are processed through denaturation, neutralization, and washing treatments following the standard protocols outlined by Ausubel et al. (Current Protocols in Molecular Biology, Greene Publishing, New York (1992)). The plaque lifts are hybridized to either radioactively labeled or non-radioactively labeled SDF DNA at room temperature for about 16 hours, usually in the presence of 50% formamide and 5× SSC (sodium chloride and sodium citrate) buffer and blocking reagents. The plaque lifts are then washed at 42° C.

with 1% Sodium Dodecyl Sulfate (SDS) and at a particular concentration of SSC. The SSC concentration used is dependent upon the stringency at which hybridization occurred in the initial Southern blot analysis performed. For example, if a fragment hybridized under medium stringency (e.g., Tm—20° C.), then this condition is maintained or preferably adjusted to a less stringent condition (e.g., Tm—30° C.) to wash the plaque lifts. Positive clones show detectable hybridization e.g., by exposure to X-ray films or chromogen formation. The positive clones are then subsequently isolated for purification using the same general protocol outlined above. Once the clone is purified, restriction analysis can be conducted to narrow the region corresponding to the gene of interest. The restriction analysis and succeeding subcloning steps can be done using procedures described by, for example, Sambrook et al. (Molecular Cloning: A Laboratory Manual, $2^{nd}$ ed. Cold Spring Harbor Laboratory Press, New York (1989)).

The procedures outlined for the lambda library are essentially similar to those used for YAC library screening, except that the YAC clones are harbored in bacterial colonies. The YAC clones are plated out at reasonable density on nitrocellulose or nylon filters supported by appropriate bacterial medium in petri plates. Following the growth of the bacterial clones, the filters are processed through the denaturation, neutralization, and washing steps following the procedures of Ausubel et al. (Current Protocols in Molecular Biology, Greene Publishing, New York (1992)). The same hybridization procedures for lambda library screening are followed.

To isolate cDNA, similar procedures using appropriately modified vectors are employed. For instance, the library can be constructed in a lambda vector appropriate for cloning cDNA such as λgt11. Alternatively, the cDNA library can be made in a plasmid vector. cDNA for cloning can be prepared by any of the methods known in the art, but is preferably prepared as described above. Preferably, a cDNA library will include a high proportion of full-length clones.

Isolating and/or Identifying Orthologous Genes

The probes and primers provided herein can be used to identify and/or isolate polynucleotides related to those set forth in Tables 1 and 2. Related polynucleotides are those that are native to other plant organisms and exhibit either similar sequence or encode polypeptides with similar biological activity. One specific example is an orthologous gene. Orthologous genes have the same functional activity. As such, orthologous genes may be distinguished from homologous genes. The percentage of identity is a function of evolutionary separation and, in closely related species, the percentage of identity can be 98 to 100%. The amino acid sequence of a protein encoded by an orthologous gene can be less than 75% identical, but tends to be at least 75% or at least 80% identical, more preferably at least 90%, most preferably at least 95% identical to the amino acid sequence of the reference protein.

To find orthologous genes, the probes are hybridized to nucleic acids from a species of interest under low stringency conditions, preferably one where sequences containing as much as 40-45% mismatches will be able to hybridize. This condition is established by $T_m$—40° C. to Tm—48° C. (see below). Blots are then washed under conditions of increasing stringency. It is preferable that the wash stringency be such that sequences that are 85 to 100% identical will hybridize. More preferably, sequences 90 to 100% identical will hybridize, and most preferably only sequences greater than 95% identical will hybridize. One of ordinary skill in the art will recognize that, due to degeneracy in the genetic code, amino acid sequences that are identical can be encoded by DNA sequences as little as 67% identical or less. Thus, it is preferable, for example, to make an overlapping series of shorter probes, on the order of 24 to 45 nucleotides, and individually hybridize them to the same arrayed library to avoid the problem of degeneracy introducing large numbers of mismatches.

As evolutionary divergence increases, genome sequences also tend to diverge. Thus, one of skill will recognize that searches for orthologous genes between more divergent species will require the use of lower stringency conditions compared to searches between closely related species. Also, degeneracy of the genetic code is more of a problem for searches in the genome of a species more distant evolutionarily from the species that is the source of the SDF probe sequences.

Therefore, the methods described by Bouckaert et al. (U.S. Provisional Patent Application Ser. No. 60/121,700; filed Feb. 25, 1999 and hereby incorporated in its entirety by reference) can be applied to the SDFs provided herein to isolate related genes from plant species which do not hybridize to the corn *Arabidopsis*, soybean, rice, wheat, and other plant sequences provided in Tables 1 and 2.

Identification of the relationship of nucleotide or amino acid sequences among plant species can be done by comparing the nucleotide or amino acid sequences of SDFs provided herein with nucleotide or amino acid sequences of other SDFs such as those provided in Table 2 of any of the priority applications.

The SDFs provided herein can also be used as probes to search for genes that are related to the SDF within a species. Such related genes are typically considered to be members of a gene family. In such a case, the sequence similarity will often be concentrated into one or a few fragments of the sequence. The fragments of similar sequence that define the gene family typically encode a fragment of a protein or RNA that has an enzymatic or structural function. The percentage of identity in the amino acid sequence of the domain that defines the gene family is preferably at least 70%, more preferably 80 to 95%, most preferably 85 to 99%. To search for members of a gene family within a species, a low stringency hybridization is usually performed, but this will depend upon the size, distribution and degree of sequence divergence of domains that define the gene family. SDFs in Table 2 of any of the priority patent applications that encompass regulatory regions can be used to identify coordinately expressed genes by using the regulatory region sequence of the SDF as a probe.

In the instances where the SDFs are identified as being expressed from genes that confer a particular phenotype, then the SDFs can also be used as probes to assay plants of different species for those phenotypes.

Methods to Inhibit Gene Expression

The nucleic acid molecules provided herein can be used to inhibit gene transcription and/or translation. Examples of such methods and materials include, without limitation, antisense constructs, ribozyme constructs, chimeraplast constructs, co-suppression, transcriptional silencing, and other methods of gene expression.

Antisense

In some instances, it is desirable to suppress expression of an endogenous or exogenous gene. A well-known instance is the FLAVOR-SAVOR™ tomato, in which the gene encoding ACC synthase is inactivated by an antisense approach, thus delaying softening of the fruit after ripening. See, for example, U.S. Pat. No. 5,859,330; U.S. Pat. No. 5,723,766; Oeller et al., *Science*, 254:437-439 (1991); and Hamilton et al., *Nature*, 346:284-287 (1990). Also, timing of flowering can be controlled by suppression of the FLOWERING LOCUS C (FLC). High levels of this transcript are associated with late flowering, while absence of FLC is associated with early flowering (Michaels et al., *Plant Cell*, 11:949 (1999)). Also, the transition of apical meristem from production of leaves with associated shoots to flowering is regulated by TERMINAL FLOWER1, APETALA1 and LEAFY. Thus, when it is desired to induce a transition from shoot production to flowering, it is desirable to suppress TFL1 expression (Liljegren, *Plant Cell*, 11:1007 (1999)). As another instance, arrested ovule development and female sterility result from suppression of the ethylene forming enzyme but can be reversed by application of ethylene (De Martinis et al., *Plant Cell*, 11:1061 (1999)). The ability to manipulate female fertility of plants is useful in increasing fruit production and creating hybrids.

In the case of polynucleotides used to inhibit expression of an endogenous gene, the introduced sequence need not be perfectly identical to a sequence of the target endogenous gene. The introduced polynucleotide sequence will typically be at least substantially identical to the target endogenous sequence.

Some polynucleotide SDFs provided herein or provided in Table 2 of any of the priority patent applications represent sequences that are expressed in corn, wheat, rice, soybean, *Arabidopsis*, and/or other plants. Any of these sequences can be used to generate antisense constructs to inhibit translation and/or degradation of transcripts of an SDFs, typically in a plant cell.

To accomplish this, a polynucleotide segment from the desired gene that can hybridize to the mRNA expressed from the desired gene (the "antisense segment") is operably linked to a promoter such that the antisense strand of RNA will be transcribed when the construct is present in a host cell. A regulated promoter can be used in the construct to control transcription of the antisense segment so that transcription occurs only under desired circumstances.

The antisense segment to be introduced generally will be substantially identical to at least a fragment of the endogenous gene or genes to be repressed. The sequence, however, need not be perfectly identical to inhibit expression. Further, the antisense product may hybridize to the untranslated region instead of or in addition to the coding sequence of the gene. The vectors provided herein can be designed such that the inhibitory effect applies to other proteins within a family of genes exhibiting homology or substantial homology to the target gene.

For antisense suppression, the introduced antisense segment sequence also need not be full length relative to either the primary transcription product or the fully processed mRNA. Generally, a higher percentage of sequence identity can be used to compensate for the use of a shorter sequence. Furthermore, the introduced sequence need not have the same intron or exon pattern, and homology of non-coding segments may be equally effective. Normally, a sequence of between about 30 or 40 nucleotides and the full length of the transcript can be used, though a sequence of at least about 100 nucleotides is preferred, a sequence of at least about 200 nucleotides is more preferred, and a sequence of at least about 500 nucleotides is especially preferred.

Chimeraplasts

The SDFs provided herein, such as those described in Table 2, can also be used to construct chimeraplasts that can be introduced into a cell to produce at least one specific nucleotide change in a sequence. A chimeraplast is an oligonucleotide comprising DNA and/or RNA that specifically hybridizes to a target region in a manner which creates a mismatched base-pair. This mismatched base-pair signals the cell's repair enzyme machinery which acts on the mismatched region resulting in the replacement, insertion, or deletion of designated nucleotide(s). The altered sequence is then expressed by the cell's normal cellular mechanisms. Chimeraplasts can be designed to repair mutant genes, modify genes, introduce site-specific mutations, and/or act to interrupt or alter normal gene function. See, e.g., U.S. Pat. Nos. 6,010,907 and 6,004,804 and PCT Publication Nos. WO99/58723 and WO99/07865.

Sense Suppression

The SDFs provided herein, such as those described in Table 2, are also useful to modulate gene expression by sense suppression. Sense suppression represents another method of gene suppression by introducing at least one exogenous copy or fragment of the endogenous sequence to be suppressed.

Introduction of expression cassettes in which a nucleic acid is configured in the sense orientation with respect to the promoter into the chromosome of a plant or by a self-replicating virus has been shown to be an effective means by which to induce degradation of mRNAs of target genes. An example of the use of this method to modulate expression of endogenous genes is provided elsewhere (Napoli et al., *The Plant Cell*, 2:279 (1990), and U.S. Pat. Nos. 5,034,323; 5,231,020; and 5,283,184). Inhibition of expression may require some transcription of the introduced sequence.

For sense suppression, the introduced sequence generally will be substantially identical to the endogenous sequence intended to be inactivated. The minimal percentage of sequence identity will typically be greater than about 65%, but a higher percentage of sequence identity might exert a more effective reduction in the level of normal gene products. Sequence identity of more than about 80% is preferred, though about 95% to absolute identity would be most preferred. As with antisense regulation, the effect would likely apply to any other proteins within a similar family of genes exhibiting homology or substantial homology to the suppressing sequence.

Transcriptional Silencing

The nucleic acid sequences provided herein or provided in Table 2 of any of the priority patent applications (and fragments thereof) contain sequences that can be inserted into the genome of an organism resulting in transcriptional silencing. Such regulatory sequences need not be operatively linked to coding sequences to modulate transcription of a gene. Specifically, a promoter sequence without any other element of a gene can be introduced into a genome to transcriptionally silence an endogenous gene (see, for example, Vaucheret et al., *The Plant Journal*, 16:651-659 (1998)). As another example, triple helices can be formed using oligonucleotides based on sequences from Table 2 provided herein or Table 2 of any of the priority patent applications, fragments thereof, and substantially similar sequence thereto. The oligonucleotide can be delivered to the host cell and can bind to the promoter in the genome to form a triple helix and prevent transcription. An oligonucleotide of interest is one that can bind to the promoter and block binding of a transcription factor to the promoter. In such a case, the oligonucleotide can be complementary to the sequences of the promoter that interact with transcription binding factors.

Other Methods to Inhibit Gene Expression

Yet another means of suppressing gene expression is to insert a polynucleotide into the gene of interest to disrupt transcription or translation of the gene.

Low frequency homologous recombination can be used to target a polynucleotide insert to a gene by flanking the polynucleotide insert with sequences that are substantially similar to the gene to be disrupted. Sequences from Table 2 provided herein or Table 2 of any of the priority patent applications, fragments thereof, and substantially similar sequence thereto can be used for homologous recombination.

In addition, random insertion of polynucleotides into a host cell genome can also be used to disrupt the gene of interest (Azpiroz-Leehan et al., *Trends in Genetics*, 13:152 (1997)). In this method, screening for clones from a library containing random insertions is preferred to identifying those that have polynucleotides inserted into the gene of interest. Such screening can be performed using probes and/or primers described above based on sequences from Table 2 provided herein or Table 2 of any of the priority patent applications, fragments thereof, and substantially similar sequence thereto. The screening can also be performed by selecting clones or $R_1$ plants having a desired phenotype.

Methods of Functional Analysis

The constructs described in the methods provided herein can be used to determine the function of the polypeptide encoded by the gene that is targeted by the constructs.

Down-regulating the transcription and translation of the targeted gene in the host cell or organisms, such as a plant, may produce phenotypic changes as compared to a wild-type cell or organism. In addition, in vitro assays can be used to determine if any biological activity, such as calcium flux, DNA transcription, nucleotide incorporation, etc. are being modulated by the down-regulation of the targeted gene.

Coordinated regulation of sets of genes, e.g., those contributing to a desired polygenic trait, is sometimes necessary to obtain a desired phenotype. SDFs provided in Table 2 or Table 2 of any of the priority patent applications and representing transcription activation and DNA binding domains can be assembled into hybrid transcriptional activators. These hybrid transcriptional activators can be used with their corresponding DNA elements (i.e., those bound by the DNA-binding SDFs) to effect coordinated expression of desired genes (Schwarz et al., *Mol. Cell. Biol.*, 12:266 (1992) and Martinez et al., *Mol. Gen. Genet.*, 261:546 (1999)).

The SDFs of the invention can also be used in the two-hybrid genetic systems to identify networks of protein-protein interactions (L. McAlister-Henn et al., *Methods* 19:330 (1999), J. C. Hu et al., *Methods* 20:80 (2000), M. Golovkin et al., *J. Biol. Chem.* 274:36428 (1999), K. Ichimura et al., *Biochem. Biophys. Res. Comm.* 253:532 (1998)). The SDFs of the invention can also be used in various expression display methods to identify important protein-DNA interactions (e.g. B. Luo et al., *J. Mol. Biol.* 266:479 (1997)).

Promoters

The SDFs provided in Table 2 or Table 2 of any of the priority patent applications are also useful as structural or regulatory sequences in a construct for modulating the expression of the corresponding gene in a plant or other organism (e.g., a symbiotic bacterium). For example, promoter sequences associated with SDFs provided in Table 2 or Table 2 of any of the priority patent applications can be useful in directing expression of coding sequences either as constitutive promoters or to direct expression in particular cell types, tissues, or organs or in response to environmental stimuli.

With respect to the SDFs provided in Table 2 or Table 2 of any of the priority patent applications, a promoter is likely to be a relatively small portion of a genomic DNA (gDNA) sequence located in the first 2000 nucleotides upstream from an initial exon identified in a gDNA sequence or initial "ATG" or methionine codon or translational start site in a corresponding cDNA sequence. Such promoters are more likely to be found in the first 1000 nucleotides upstream of an initial ATG or methionine codon or translational start site of a cDNA sequence corresponding to a gDNA sequence. In particular, the promoter is usually located upstream of the transcription start site. The fragments of a particular gDNA sequence that function as elements of a promoter in a plant cell will preferably be found to hybridize to gDNA sequences of SDFs provided in Table 2 or Table 2 of any of the priority patent applications at medium or high stringency, relevant to the length of the probe and its base composition.

Promoters are generally modular in nature. Promoters can consist of a basal promoter that functions as a site for assembly of a transcription complex comprising an RNA polymerase (e.g., RNA polymerase II). A typical transcription complex will include additional factors such as $TF_{II}B$, $TF_{II}D$, and $TF_{II}E$. Of these, $TF_{II}D$ appears to be the only one to bind DNA directly. The promoter might also contain one or more enhancers and/or suppressors that function as binding sites for additional transcription factors that have the function of modulating the level of transcription with respect to tissue specificity and of transcriptional responses to particular environmental or nutritional factors, and the like.

Short DNA sequences representing binding sites for proteins can be separated from each other by intervening sequences of varying length. For example, within a particular functional module, protein binding sites may be constituted by regions of 5 to 60, preferably 10 to 30, more preferably 10 to 20 nucleotides. Within such binding sites, there are typically 2 to 6 nucleotides that specifically contact amino acids of the nucleic acid binding protein. The protein binding sites are usually separated from each other by 10 to several hundred nucleotides, typically by 15 to 150 nucleotides, often by 20 to 50 nucleotides. DNA binding sites in promoter elements often display dyad symmetry in their sequence. Often elements binding several different proteins, and/or a plurality of sites that bind the same protein, will be combined in a region of 50 to 1,000 basepairs.

Elements that have transcription regulatory function can be isolated from their corresponding endogenous gene, or the desired sequence can be synthesized, and recombined in constructs to direct expression of a coding region of a gene in a desired tissue-specific, temporal-specific, or other desired manner of inducibility or suppression. When hybridizations are performed to identify or isolate elements of a promoter by hybridization to the long sequences presented in Table 2 provided herein or Table 2 of any of the priority patent applications, conditions are adjusted to account for the above-described nature of promoters. For example short probes, constituting the element sought, are preferably used under low temperature and/or high salt conditions. When long probes, which might include several promoter elements, are used or when hybridizing to promoters across species, low to medium stringency conditions are preferred.

If a nucleotide sequence of an SDF such as those provided in Table 2 of any of the priority patent applications, or part of the SDF, functions as a promoter or fragment of a promoter, then nucleotide substitutions, insertions, or deletions that do not substantially affect the binding of relevant DNA binding proteins would be considered equivalent to the exemplified nucleotide sequence. It is envisioned that there are instances where it is desirable to decrease the binding of relevant DNA binding proteins to silence or down-regulate a promoter, or conversely to increase the binding of relevant DNA binding proteins to enhance or up-regulate a promoter. In such instances, polynucleotides representing changes to the nucleotide sequence of the DNA-protein contact region by insertion of additional nucleotides, by changes to identity of relevant nucleotides, including use of chemically-modified bases, or by deletion of one or more nucleotides are considered encompassed by the present invention. In addition, fragments of the promoter sequences described in Table 2 of any of the priority patent applications and variants thereof can be fused with other promoters or fragments to facilitate transcription and/or transcription in specific type of cells or under specific conditions.

Promoter function can be assayed by methods known in the art, preferably by measuring activity of a reporter gene operatively linked to the sequence being tested for promoter function. Examples of reporter genes include those encoding luciferase, green fluorescent protein, GUS, neo, cat, and bar.

UTRs and Junctions

Polynucleotides comprising untranslated (UTR) sequences and intron/exon junctions are also within the scope of the invention. UTR sequences include introns and 5' or 3' untranslated regions (5' UTRs or 3' UTRs). Fragments of the sequences shown in Table 2 can comprise UTRs and intron/exon junctions.

These fragments of SDFs, especially UTRs, can have regulatory functions related to, for example, translation rate and mRNA stability. Thus, these fragments of SDFs can be isolated for use as elements of gene constructs for regulated production of polynucleotides encoding desired polypeptides.

Introns of genomic DNA segments might also have regulatory functions. Sometimes regulatory elements, especially transcription enhancer or suppressor elements, are found within introns. Also, elements related to stability of heteronuclear RNA and efficiency of splicing and of transport to the cytoplasm for translation can be found in intron elements. Thus, these segments can also find use as elements of expression vectors intended for use to transform plants.

Just as with promoters, UTR sequences and intron/exon junctions can vary from those shown in Table 2 provided herein or Table 2 of any of the priority patent applications. Such changes from those sequences preferably will not affect the regulatory activity of the UTRs or intron/exon junction sequences on expression, transcription, or translation unless selected to do so. However, in some instances, down- or up-regulation of such activity may be desired to modulate traits or phenotypic or in vitro activity.

Coding Sequences

Isolated polynucleotides of the invention can include coding sequences that encode polypeptides comprising an amino acid sequence encoded by sequences described in Table 1 or 2 or an amino acid sequence presented in Table 1 or 2.

A nucleotide sequence encodes a polypeptide if a cell (or a cell free in vitro system) expressing that nucleotide sequence produces a polypeptide having the recited amino acid sequence when the nucleotide sequence is transcribed and the primary transcript is subsequently processed and translated by a host cell (or a cell free in vitro system) harboring the nucleic acid. Thus, an isolated nucleic acid that encodes a particular amino acid sequence can be a genomic sequence comprising exons and introns or a cDNA sequence that represents the product of splicing thereof. An isolated nucleic acid encoding an amino acid sequence also encompasses heteronuclear RNA, which contains sequences that are spliced out during expression, and mRNA, which lacks those sequences.

Coding sequences can be constructed using chemical synthesis techniques or by isolating coding sequences or by modifying such synthesized or isolated coding sequences as described above.

In addition to coding sequences encoding the polypeptide sequences of Table 1 or 2, which can be native to corn, *Arabidopsis*, soybean, rice, wheat, and other plants, the isolated polynucleotides can be polynucleotides that encode variants, fragments, and fusions of those native proteins. Such polypeptides are described below.

In variant polynucleotides generally, the number of substitutions, deletions, or insertions is preferably less than 20%; more preferably less than 15%; and even more preferably less than 10%, 5%, 3%, or 1% of the number of nucleotides comprising a particularly exemplified sequence. It is generally expected that non-degenerate nucleotide sequence changes that result in 1 to 10, more preferably 1 to 5, and most preferably 1 to 3 amino acid insertions, deletions, or substitutions will not greatly affect the function of an encoded polypeptide. The most preferred embodiments are those wherein 1 to 20, preferably 1 to 10, most preferably 1 to 5 nucleotides are added to, or deleted from and/or substituted in the sequences disclosed in Table 1 or 2, or polynucleotides that encode polypeptides disclosed in Table 1 or 2, or fragments thereof.

Insertions or deletions in polynucleotides intended to be used for encoding a polypeptide preferably preserve the reading frame. This consideration is not so important in instances when the polynucleotide is intended to be used as a hybridization probe.

Native Polypeptides and Proteins

Polypeptides within the scope of the invention include both native proteins as well as variants, fragments, and fusions thereof. Polypeptides of the invention are those encoded by any of the six reading frames of sequences shown in Table 1 or 2, preferably encoded by the three frames reading in the 5' to 3' direction of the sequences as shown.

Native polypeptides include the proteins encoded by the sequences shown in Table 1 or 2. Such native polypeptides include those encoded by allelic variants.

Polypeptide and protein variants will exhibit at least 75% sequence identity to those native polypeptides of Table 1 or 2. More preferably, the polypeptide variants will exhibit at least 85% sequence identity, at least 90% sequence identity, or at least 95%, 96%, 97%, 98%, or 99% sequence identity. Fragments of polypeptide or fragments of polypeptides will exhibit similar percentages of sequence identity to the relevant fragments of the native polypeptide. Fusions will exhibit a similar percentage of sequence identity in that fragment of the fusion represented by the variant of the native peptide.

Polypeptide and protein variants of the invention can exhibit at least 75% sequence identity to those motifs or consensus sequences provided herein. More preferably, the polypeptide variants can exhibit at least 85% sequence identity; at least 90% sequence identity; or at least 95%, 96%, 97%, 98%, or 99% sequence identity. Fragments of polypeptides can exhibit similar percentages of sequence identity to the relevant fragments of the native polypeptide. Fusions will exhibit a similar percentage of sequence identity in that fragment of the fusion represented by the variant of the native peptide.

Furthermore, polypeptide variants will exhibit at least one of the functional properties of the native protein. Such properties include, without limitation, protein interaction, DNA interaction, biological activity, immunological activity, receptor binding, signal transduction, transcription activity, growth factor activity, secondary structure, three-dimensional structure, etc. As to properties related to in vitro or in vivo activities, the variants preferably exhibit at least 60% of the activity of the native protein; more preferably at least 70%, even more preferably at least 80%, 85%, 90% or 95% of at least one activity of the native protein.

One type of variant of native polypeptides comprises amino acid substitutions, deletions, and/or insertions. Conservative substitutions are preferred to maintain the function or activity of the polypeptide.

Within the scope of percentage of sequence identity described above, a polypeptide of the invention may have additional individual amino acids or amino acid sequences inserted into the polypeptide in the middle thereof and/or at the N-terminal and/or C-terminal ends thereof. Likewise, some of the amino acids or amino acid sequences may be deleted from the polypeptide.

Antibodies

Isolated polypeptides can be utilized to produce antibodies. Polypeptides of the invention can generally be used, for example, as antigens for raising antibodies by known techniques. The resulting antibodies are useful as reagents for determining the distribution of the antigen protein within the tissues of a plant or within a cell of a plant. The antibodies are also useful for examining the production level of proteins in various tissues, for example in a wild-type plant or following genetic manipulation of a plant, by methods such as Western blotting.

Antibodies of the present invention, both polyclonal and monoclonal, may be prepared by conventional methods. In general, the polypeptides of the invention are first used to immunize a suitable animal, such as a mouse, rat, rabbit, or goat. Rabbits and goats are preferred for the preparation of polyclonal sera due to the volume of serum obtainable, and the availability of labeled anti-rabbit and anti-goat antibodies as detection reagents. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization.

Polyclonal antisera is obtained by bleeding the immunized animal into a glass or plastic container, incubating the blood at 25° C. for one hour, followed by incubating the blood at 4° C. for 2-18 hours. The serum is recovered by centrifugation (e.g., 1,000×g for 10 minutes). About 20-50 mL per bleed may be obtained from rabbits.

Monoclonal antibodies are prepared using the method of Kohler and Milstein (Nature, 256: 495 (1975)), or modification thereof. Typically, a mouse or rat is immunized as described above. However, rather than bleeding the animal to extract serum, the spleen (and optionally several large lymph nodes) is removed and dissociated into single cells. If desired, the spleen cells can be screened (after removal of nonspecifically adherent cells) by applying a cell suspension to a plate, or well, coated with the protein antigen. B-cells producing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (as ascites in mice).

Other methods for sustaining antibody-producing B-cell clones, such as by EBV transformation, are known.

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TNB) to a blue pigment, quantifiable with a spectrophotometer.

Variants

A type of variant of the native polypeptides comprises amino acid substitutions. Conservative substitutions, described above, are preferred to maintain the function or activity of the polypeptide. Such substitutions include conservation of charge, polarity, hydrophobicity, size, etc. For example, one or more amino acid residues within the sequence can be substituted with another amino acid of similar polarity that acts as a functional equivalent, for example providing a hydrogen bond in an enzymatic catalysis. Substitutes for an amino acid within an exemplified sequence are preferably made among the members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid.

Within the scope of percentage of sequence identity described above, a polypeptide of the invention may have additional individual amino acids or amino acid sequences inserted into the polypeptide in the middle thereof and/or at the N-terminal and/or C-terminal ends thereof. Likewise, some of the amino acids or amino acid sequences may be deleted from the polypeptide. Amino acid substitutions may also be made in the sequences; conservative substitutions being preferred.

One preferred class of variants are those that comprise (1) the domain of an encoded polypeptide and/or (2) residues conserved between the encoded polypeptide and related polypeptides. For this class of variants, the encoded polypeptide sequence is changed by insertion, deletion, or substitution at positions flanking the domain and/or conserved residues.

Another class of variants includes those that comprise an encoded polypeptide sequence that is changed in the domain or conserved residues by a conservative substitution.

Yet another class of variants includes those that lack one of the in vitro activities, or structural features of the encoded polypeptides. One example is polypeptides or proteins produced from genes comprising dominant negative mutations. Such a variant may comprise an encoded polypeptide sequence with non-conservative changes in a particular domain or group of conserved residues.

Fragments

Fragments of particular interest are those that comprise a domain identified for a polypeptide encoded by an MLS of the instant invention and variants thereof. Also, fragments that comprise at least one region of residues conserved between an MLS encoded polypeptide and its related polypeptides are of interest. Fragments are sometimes useful as polypeptides corresponding to genes comprising dominant negative mutations.

Fusions

Of interest are chimeras comprising (1) a fragment of the MLS encoded polypeptide or variants thereof of interest and (2) a fragment of a polypeptide comprising the same domain. For example, an AP2 helix encoded by a MLS provided in Table 2 of any of the priority patent applications can be fused to a second AP2 helix from ANT protein, which comprises two AP2 helices. The present invention also encompasses fusions of MLS encoded polypeptides, variants, or fragments thereof fused with related proteins or fragments thereof.

Definition of Domains

The polypeptides of the invention can possess identifying domains as indicated in Table 1. Domains are fingerprints or signatures that can be used to characterize protein families and/or motifs. Such fingerprints or signatures can comprise conserved (1) primary sequence, (2) secondary structure, and/or (3) three-dimensional conformation. Generally, each domain has been associated with either a family of proteins or a motif. Typically, these families and motifs have been correlated with specific in vitro and/or in vivo activities. Usually, the polypeptides with designated domain(s) can exhibit at least one activity that is exhibited by any polypeptide that comprises the same domain(s).

Specific domains within the MLS-encoded polypeptides can be indicated in Table 1. In addition, the domains with the MLS-encoded-polypeptide can be defined by the region that exhibits at least 70% sequence identity with a consensus sequence. Protein domain descriptions can be obtained from Prosite (Internet site: "expasy" dot "ch" slash "prosite" slash) (contains 1030 documentation entries that describe 1366 different patterns, rules and profiles/matrices), and Pfam (Internet site: "pfam" dot "wustl" dot "edu" slash "browse" dot "shtml").

The particular sequences of identified SDFs can be provided in Table 2. One of ordinary skill in the art, having this data, can obtain cloned DNA fragments, synthetic DNA fragments or polypeptides constituting desired sequences by recombinant methodology known in the art.

Methods of Modulating Polypeptide Production

It is contemplated that polynucleotides provided herein can be incorporated into a host cell or in vitro system to modulate polypeptide production. For instance, the SDFs prepared as described herein can be used to prepare expression cassettes useful in a number of techniques for suppressing or enhancing expression.

An example are polynucleotides comprising sequences to be transcribed, such as coding sequences of the present invention, can be inserted into nucleic acid constructs to modulate polypeptide production. Typically, such sequences to be transcribed are heterologous to at least one element of the nucleic acid construct to generate a chimeric gene or construct.

Another example of useful polynucleotides are nucleic acid molecules comprising regulatory sequences provided in Table 2 of any of the priority patent applications. Chimeric genes or constructs can be generated when the regulatory sequences are linked to heterologous sequences in a vector construct. Within the scope of invention are such chimeric gene and/or constructs.

Also within the scope of the invention are nucleic acid molecules, whereof at least a part or fragment of these DNA molecules are presented in Table 1 or 2 or polynucleotide encoding polypeptides presented in Table 1 or 2, and wherein the coding sequence is under the control of its own promoter and/or its own regulatory elements. Such molecules are useful for transforming the genome of a host cell or an organism regenerated from said host cell for modulating polypeptide production.

Additionally, a vector capable of producing the oligonucleotide can be inserted into the host cell to deliver the oligonucleotide.

More detailed description of components to be included in vector constructs are described both above and below.

Whether the chimeric vectors or native nucleic acids are utilized, such polynucleotides can be incorporated into a host cell to modulate polypeptide production. Native genes and/or nucleic acid molecules can be effective when exogenous to the host cell.

Methods of modulating polypeptide expression includes, without limitation, suppression methods (such as antisense methods, ribozyme methods, co-suppression methods, methods involving inserting sequences into the gene to be modulated, and methods involving regulatory sequence modulation) as well as methods for enhancing production (such as methods involving inserting exogenous sequences and methods involving regulatory sequence modulation).

Suppression

Expression cassettes provided herein can be used to suppress expression of endogenous genes which comprise the SDF sequence. Inhibiting expression can be useful, for instance, to tailor the ripening characteristics of a fruit (Oeller et al., *Science,* 254:437 (1991)) or to influence seed size (WO 98/07842) or to provoke cell ablation (Mariani et al., *Nature,* 357: 384-387 (1992)).

As described above, a number of methods can be used to inhibit gene expression in plants, such as antisense, ribozyme, introduction of exogenous genes into a host cell, insertion of a polynucleotide sequence into the coding sequence and/or the promoter of the endogenous gene of interest, and the like.

Antisense

An expression cassette as described above can be transformed into host cell or plant to produce an antisense strand of RNA. For plant cells, antisense RNA inhibits gene expression by preventing the accumulation of mRNA which encodes the enzyme of interest, see, e.g., Sheehy et al., *Proc. Nat. Acad. Sci. USA,* 85:8805 (1988), and Hiatt et al., U.S. Pat. No. 4,801,540.

Co-Suppression

Another method of suppression is by introducing an exogenous copy of the gene to be suppressed. Introduction of expression cassettes in which a nucleic acid is configured in the sense orientation with respect to the promoter has been shown to prevent the accumulation of mRNA. A detailed description of this method is described above.

Insertion of Sequences into the Gene to be Modulated

Yet another means of suppressing gene expression is to insert a polynucleotide into the gene of interest to disrupt transcription or translation of the gene.

Homologous recombination could be used to target a polynucleotide insert to a gene using the Cre-Lox system (Vergunst et al., *Nucleic Acids Res.*, 26:2729 (1998); Vergunst et al., *Plant Mol. Biol.*, 38:393 (1998) and Albert et al., *Plant J.*, 7:649 (1995)).

In addition, random insertion of polynucleotides into a host cell genome can also be used to disrupt the gene of interest (Azpiroz-Leehan et al., *Trends in Genetics*, 13:152 (1997)). In this method, screening for clones from a library containing random insertions is preferred for identifying those that have polynucleotides inserted into the gene of interest. Such screening can be performed using probes and/or primers described above based on sequences from Table 1 or 2 provided herein or Table 1 or 2 of any of the priority patent applications, polynucleotides encoding polypeptides set forth in Table 1 or 2 provided herein or Table 1 or 2 of any of the priority patent applications, fragments thereof, and substantially similar sequence thereto. The screening can also be performed by selecting clones or any transgenic plants having a desired phenotype.

Genes Comprising Dominant-Negative Mutations

When suppression of production of the endogenous, native protein is desired it is often helpful to express a gene comprising a dominant negative mutation. Production of protein variants produced from genes comprising dominant negative mutations is a useful tool for research. Genes comprising dominant negative mutations can produce a variant polypeptide which is capable of competing with the native polypeptide, but which does not produce the native result. Consequently, over expression of genes comprising these mutations can titrate out an undesired activity of the native protein. For example, the product from a gene comprising a dominant negative mutation of a receptor can be used to constitutively activate or suppress a signal transduction cascade, allowing examination of the phenotype and thus the trait(s) controlled by that receptor and pathway. Alternatively, the protein arising from the gene comprising a dominant-negative mutation can be an inactive enzyme still capable of binding to the same substrate as the native protein and therefore competes with such native protein.

Products from genes comprising dominant-negative mutations can also act upon the native protein itself to prevent activity. For example, the native protein may be active only as a homo-multimer or as one subunit of a hetero-multimer. Incorporation of an inactive subunit into the multimer with native subunit(s) can inhibit activity.

Thus, gene function can be modulated in host cells of interest by insertion into these cells vector constructs comprising a gene comprising a dominant-negative mutation.

Enhanced Expression

Enhanced expression of a gene of interest in a host cell can be accomplished by either (1) insertion of an exogenous gene or (2) promoter modulation.

Insertion of an Exogenous Gene

Insertion of an expression construct encoding an exogenous gene can boost the number of gene copies expressed in a host cell.

Such expression constructs can comprise genes that either encode the native protein that is of interest or that encode a variant that exhibits enhanced activity as compared to the native protein.

Such genes encoding proteins of interest can be constructed from the sequences from Table 1 or 2 provided herein or Table 1 or 2 of any of the priority patent applications, polynucleotides encoding polypeptides set forth in Table 1 or 2 provided herein or Table 1 or 2 of any of the priority patent applications, fragments thereof, and substantially similar sequence thereto.

Such an exogenous gene can include either a constitutive promoter permitting expression in any cell in a host organism or a promoter that directs transcription only in particular cells or times during a host cell life cycle or in response to environmental stimuli.

Gene Constructs and Vector Construction

To use isolated SDFs of the present invention or a combination of them or parts and/or mutants and/or fusions of said SDFs in the above techniques, recombinant DNA vectors which comprise said SDFs and are suitable for transformation of cells, such as plant cells, are usually prepared. The SDF construct can be made using standard recombinant DNA techniques (Sambrook et al., Molecular Cloning, a Laboratory Manual, 2nd ed., c. 1989 by Cold Spring Harbor Laboratory Press, Cold Spring Harbor, N.Y.) and can be introduced to the species of interest by *Agrobacterium*-mediated transformation or by other means of transformation (e.g., particle gun bombardment) as referenced below.

The vector backbone can be any of those typical in the art such as plasmids, viruses, artificial chromosomes, BACs, YACs, PACs, and vectors of the sort described by (a) BAC: Shizuya et al., *Proc. Natl. Acad. Sci. USA*, 89:8794-8797 (1992); and Hamilton et al., *Proc. Natl. Acad. Sci. USA*, 93:9975-9979 (1996);

(b) YAC: Burke et al., *Science*, 236:806-812 (1987);

(c) PAC: Stemberg et al., *Proc. Natl. Acad. Sci. USA, January;* 87(1):103-7 (1990);

(d) Bacteria-Yeast Shuttle Vectors: Bradshaw et al., *Nucl. Acids. Res.*, 23:4850-4856 (1995);

(e) Lambda Phage Vectors: Replacement Vector, e.g., Frischauf et al., *J. Mol. Biol.*, 170:827-842 (1983) or Insertion vector, e.g., Huynh et al., In: Glover NM (ed) DNA Cloning: A practical Approach, Vol. 1 Oxford: IRL Press (1985);

(f) T-DNA gene fusion vectors: Walden et al., *Mol. Cell. Biol.*, 1:175-194 (1990); and (g) Plasmid vectors: Sambrook et al., Molecular Cloning, a Laboratory Manual, 2nd ed., c. 1989 by Cold Spring Harbor Laboratory Press, Cold Spring Harbor, N.Y.

Typically, a vector will comprise the exogenous gene, which in turn comprises an SDF of the present invention to be introduced into the genome of a host cell, and which gene may be an antisense construct, a ribozyme construct, chimeraplast, or a coding sequence with any desired transcriptional and/or translational regulatory sequences, such as promoters, UTRs, and 3' end termination sequences. Vectors of the invention can also include origins of replication, scaffold attachment regions (SARs), markers, homologous sequences, introns, etc.

A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for over-expression, a plant promoter fragment may be employed that will direct transcription of the gene in all tissues of a regenerated plant. Alternatively, the plant promoter may direct transcription of an SDF of the invention in a specific tissue (tissue-specific promoters) or may be otherwise under more precise environmental control (inducible promoters).

If proper polypeptide production is desired, a polyadenylation region at the 3'-end of the coding region is typically included. The polyadenylation region can be derived from the natural gene, from a variety of other plant genes, or from T-DNA.

The vector comprising the sequences from genes or SDF or the invention may comprise a marker gene that confers a selectable phenotype on plant cells. The vector can include promoter and coding sequence, for instance. For example, the marker may encode biocide resistance, particularly antibiotic resistance, such as resistance to kanamycin, G418, bleomycin, hygromycin, or herbicide resistance, such as resistance to chlorosulfuron or phosphinotricin.

Coding Sequences

Generally, the sequence in the transformation vector and to be introduced into the genome of the host cell does not need to be absolutely identical to an SDF of the present invention. Also, it is not necessary for it to be full length, relative to either the primary transcription product or fully processed mRNA. Furthermore, the introduced sequence need not have the same intron or exon pattern as a native gene. Also, heterologous non-coding segments can be incorporated into the coding sequence without changing the desired amino acid sequence of the polypeptide to be produced.

Promoters

As explained above, introducing an exogenous SDF from the same species or an orthologous SDF from another species are useful to modulate the expression of a native gene corresponding to that SDF of interest. Such an SDF construct can be under the control of either a constitutive promoter or a highly regulated inducible promoter (e.g., a copper inducible promoter). The promoter of interest can initially be either endogenous or heterologous to the species in question. When re-introduced into the genome of said species, such promoter becomes exogenous to said species. Over-expression of an SDF transgene can lead to co-suppression of the homologous endogenous sequence thereby creating some alterations in the phenotypes of the transformed species as demonstrated by similar analysis of the chalcone synthase gene (Napoli et al., *Plant Cell*, 2:279 (1990) and van der Krol et al., *Plant Cell*, 2:291 (1990)). If an SDF is found to encode a protein with desirable characteristics, its over-production can be controlled so that its accumulation can be manipulated in an organ- or tissue-specific manner utilizing a promoter having such specificity.

Likewise, if the promoter of an SDF (or an SDF that includes a promoter) is found to be tissue-specific or developmentally regulated, such a promoter can be utilized to drive or facilitate the transcription of a specific gene of interest (e.g., seed storage protein or root-specific protein). Thus, the level of accumulation of a particular protein can be manipulated or its spatial localization in an organ- or tissue-specific manner can be altered.

Signal Peptides

SDFs containing signal peptides are indicated in Table 1 or 2 of any of the priority patent applications. In some cases, it may be desirable for the protein encoded by an introduced exogenous or orthologous SDF to be targeted (1) to a particular organelle intracellular compartment, (2) to interact with a particular molecule such as a membrane molecule, or (3) for secretion outside of the cell harboring the introduced SDF. This will be accomplished using a signal peptide.

Signal peptides direct protein targeting, are involved in ligand-receptor interactions, and act in cell to cell communication. Many proteins, especially soluble proteins, contain a signal peptide that targets the protein to one of several different intracellular compartments. In plants, these compartments include, but are not limited to, the endoplasmic reticulum (ER), mitochondria, plastids (such as chloroplasts), the vacuole, the Golgi apparatus, protein storage vesicles (PSV) and, in general, membranes. Some signal peptide sequences are conserved, such as the Asn-Pro-Ile-Arg amino acid motif found in the N-terminal propeptide signal that targets proteins to the vacuole (Marty, *The Plant Cell*, 11:587-599 (1999)). Other signal peptides do not have a consensus sequence per se, but are largely composed of hydrophobic amino acids, such as those signal peptides targeting proteins to the ER (Vitale and Denecke, *The Plant Cell*, 11:615-628 (1999)). Still others do not appear to contain either a consensus sequence or an identified common secondary sequence, for instance the chloroplast stromal targeting signal peptides (Keegstra and Cline, *The Plant Cell*, 11:557-570 (1999)). Furthermore, some targeting peptides are bipartite, directing proteins first to an organelle and then to a membrane within the organelle (e.g., within the thylakoid lumen of the chloroplast; see Keegstra and Cline, *The Plant Cell*, 11:557-570 (1999)). In addition to the diversity in sequence and secondary structure, placement of the signal peptide is also varied. Proteins destined for the vacuole, for example, have targeting signal peptides found at the N-terminus, at the C-terminus, and at a surface location in mature, folded proteins. Signal peptides also serve as ligands for some receptors.

These characteristics of signal proteins can be used to more tightly control the phenotypic expression of introduced SDFs. In particular, associating the appropriate signal sequence with a specific SDF can allow sequestering of the protein in specific organelles (plastids, as an example), secretion outside of the cell, targeting interaction with particular receptors, etc. Hence, the inclusion of signal proteins in constructs involving SDFs increases the range of manipulation of SDF phenotypic expression. The nucleotide sequence of the signal peptide can be isolated from characterized genes using common molecular biological techniques or can be synthesized in vitro.

In addition, the native signal peptide sequences, both amino acid and nucleotide, described in Table 1 or 2 provided herein or Table 1 or 2 of any priority patent application can be used to modulate polypeptide transport. Further variants of the native signal peptides described in Table 1 or 2 provided herein or Table 1 or 2 of any priority patent application are contemplated. Insertions, deletions, or substitutions can be made. Such variants will retain at least one of the functions of the native signal peptide as well as exhibiting some degree of sequence identity to the native sequence.

Also, fragments of the signal peptides of the invention are useful and can be fused with other signal peptides of interest to modulate transport of a polypeptide.

Transformation Techniques

A wide range of techniques for inserting exogenous polynucleotides are known for a number of host cells, including, without limitation, bacterial, yeast, mammalian, insect and plant cells.

Techniques for transforming a wide variety of higher plant species are well known and described in the technical and scientific literature. See, e.g. Weising et al., *Ann. Rev. Genet.*, 22:421 (1988), and Christou, *Euphytica*, v. 85, n. 1-3:13-27, (1995).

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria (McCornac et al., *Mol. Biotechnol.*, 8:199 (1997); Hamilton, *Gene*, 200:107 (1997); Salomon et al., *EMBO J.*, 3:141 (1984); Herrera-Estrella et al., *EMBO J.* 2:987 (1983).

Microinjection techniques are known in the art and well described in the scientific and patent literature. The introduction of DNA constructs using polyethylene glycol precipitation is described by Paszkowski et al. (*EMBO J.*, 3:2717 (1984)). Electroporation techniques are described by Fromm et al. (*Proc. Natl. Acad. Sci. USA*, 82:5824 (1985)). Ballistic transformation techniques are described by Klein et al. (*Nature*, 327:773 (1987)). *Agrobacterium tumefaciens*-mediated transformation techniques, including disarming and use of binary or co-integrate vectors, are well described in the scientific literature. See, for example, Hamilton, *Gene*, 200:107 (1997); Müller et al., *Mol. Gen. Genet.*, 207:171 (1987); Komari et al., *Plant J.*, 10:165 (1996); Venkateswarlu et al., *Biotechnology*, 9:1103 (1991); Gleave, *Plant Mol. Biol.*, 20:1203 (1992); Graves and Goldman, *Plant Mol. Biol.*, 7:34 (1986); and Gould et al., *Plant Physiology*, 95:426 (1991).

Transformed plant cells which are derived by any of the above transformation techniques can be cultured to regenerate a whole plant that possesses the transformed genotype and thus the desired phenotype such as seedlessness. Such regeneration techniques rely on manipulation of certain phytohormones in a tissue culture growth medium, typically relying on a biocide and/or herbicide marker, which has been introduced together with the desired nucleotide sequences. Plant regeneration from cultured protoplasts is described elsewhere (Evans et al., *Protoplasts Isolation and Culture* in "Handbook of Plant Cell Culture," pp. 124-176, MacMillan Publishing Company, New York, 1983; and Binding, *Regeneration of Plants, Plant Protoplasts*, pp. 21-73, CRC Press, Boca Raton, 1988). Regeneration can also be obtained from plant callus, explants, organs, or parts thereof. Such regeneration techniques are described generally by Klee et al. (*Ann. Rev. of Plant Phys.*, 38:467 (1987)). Regeneration of monocots (rice) is described by Hosoyama et al. (*Biosci. Biotechnol. Biochem.*, 58:1500 (1994)) and by Ghosh et al. (*J. Biotechnol.*, 32:1 (1994)). The nucleic acids of the invention can be used to confer desired traits on essentially any plant.

Thus, the invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea.*

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Definitions

"Percentage of sequence identity" as used herein is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman, (*Add. APL. Math.*, 2:482 (1981)), by the homology alignment algorithm of Needleman and Wunsch (*J. Mol. Biol.*, 48:443 1970), by the search for similarity method of Pearson and Lipman (*Proc. Natl. Acad. Sci. USA,* 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

"Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$—5° C. to $T_m$—10° C. Medium or moderate stringency conditions are those providing $T_m$—20° C. to $T_m$—29° C. Low stringency conditions are those providing a condition of $T_m$—40° C. to $T_m$—48° C. The relationship of hybridization conditions to $T_m$ (in ° C.) is expressed in the mathematical equation:

$$T_m = 81.5 - 16.6(\log_{10}[\text{Na}^+]) + 0.41(\% \, G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[\text{Na}^+]/(1+0.7[\text{Na}^+])\} + 0.41(\% \, G+C) - 500/L \, 0.63(\% \text{ formamide}) \quad (2)$$

where L is the length of the probe in the hybrid. (P. Tijessen, "Hybridization with Nucleic Acid Probes" in Laboratory Techniques in Biochemistry and Molecular Biology, P. C. vand der Vliet, ed., c. 1993 by Elsevier, Amsterdam). The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., *J. Mol. Biol.*, 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$, and low stringency is 45-48° C. below $T_m$.

SEQUENCE LISTING

<160> NUMBER OF SEQ ID NOS: 4

<210> SEQ ID NO 1
<211> LENGTH: 1503
<212> TYPE: DNA
<213> ORGANISM: Arabidopsis thaliana
<220> FEATURE:
<221> NAME/KEY: misc_feature
<222> LOCATION: (1)...(1503)
<223> OTHER INFORMATION: Ceres Seq ID no. 2158130

<400> SEQUENCE: 1

```
atgtcgatct ctctctattt cctttgctc ttgcctctct ttttaatctt cttcaaaaag      60
ctctcacctt ctaaaggaaa gcttcctcct ggacctctag gtcttccgat tatcgggaac     120
ttgcaccaac ttggaaaatc tctccataga tcttttcata aactttctca aaactatgga     180
cccgtgatgt ttctacattt cggtgtggtc cctgtggttg tggtctccac aagagaagca     240
gctgaagaag ttctcaagac tcatgatctc gagacttgta cccgaccaaa gctaacagcg     300
accaaattgt tttcttacaa ctacaaagac attggcttcg ctcaatacgg tgatgactgg     360
agagagatga ggaagcttgc gatgctcgag cttttagct cgaaaaagct caaggctttc     420
aggtatatta gagaagaaga gagtgaagtc ctagtcaata aactctcgaa atctgctgag     480
acacgaacta tggtagactt gagaaaagct cttttctctt ataccgctag tatcgtatgt     540
agactcgctt ttggacagaa cttccatgag tgcgattttg tcgatatgga taaagttgaa     600
gatcttgtgc tcgaatctga gaccaatctt ggctcattcg cgttcactga cttcttcccc     660
gcaggtcttg ggtgggttat agaccggatc tctggccaac attcggagtt gcacaaagcc     720
tttgctagac ttagtaattt ctttcaacat gtgatcgatg atcacttgaa gcccgggcaa     780
tctcaagatc attcagacat cattggtgtc atgttagata tgatcaataa agagagtaaa     840
gtcggttcct tccaagtcac ctacgaccat cttaaaggag tcatgtcgga tgtgtttta     900 gcgggagtga acgcaggagc gatcacaatg atatgggcga tgacagagct agccagacat     960
ccgagagtga tgaagaaact tcaacaagag attcgagaaa tactcggaga caacaaagaa    1020
aaaatcacgg aacaagatct cgaaaaggtt cactacttga aacttgtgat cgaagaaaca    1080
ttcagattac atcctccagc tcctctcttg ctacctagag agacaatgtc tgacttaaag    1140
attcaaggct acaatattcc caagaacacg atgatagaga tcaatactta ttcaatagga    1200
cgcgatccta attgctggga aaaccctaac gatttcaacc cggagagatt tatcgatagc    1260
cctgtcgaat ataagggtca acattacgag ttgttgcctt tggtgctgg tcgcaggatt    1320 tgtccaggaa tggctacggg gataactatc gtcgagctcg gtttacttaa tgttctttac    1380 ttcttttgatt ggagtttgcc tgatggaatg aaaattgaag acatagacat ggaagaagct    1440
ggagctttcg tcgtcgccaa gaaagtccct cttgagctga ttccaactcc acatcagtgg    1500
``` tga                                                              1503

<210> SEQ ID NO 2
<211> LENGTH: 500
<212> TYPE: PRT
<213> ORGANISM: Arabidopsis thaliana
<220> FEATURE:
<221> NAME/KEY: PEPTIDE
<222> LOCATION: (1)...(500)
<223> OTHER INFORMATION: Ceres Seq. ID no. 2158131

<400> SEQUENCE: 2

```
Met Ser Ile Ser Leu Tyr Phe Leu Leu Leu Pro Leu Phe Leu Ile
 1               5                  10                  15

Phe Phe Lys Lys Leu Ser Pro Ser Lys Gly Lys Leu Pro Pro Gly Pro
            20                  25                  30

Leu Gly Leu Pro Ile Ile Gly Asn Leu His Gln Leu Gly Lys Ser Leu
        35                  40                  45

His Arg Ser Phe His Lys Leu Ser Gln Asn Tyr Gly Pro Val Met Phe
    50                  55                  60

Leu His Phe Gly Val Val Pro Val Val Val Ser Thr Arg Glu Ala
65                  70                  75                  80

Ala Glu Val Leu Lys Thr His Asp Leu Glu Thr Cys Thr Arg Pro
                85                  90                  95

Lys Leu Thr Ala Thr Lys Leu Phe Ser Tyr Asn Tyr Lys Asp Ile Gly
            100                 105                 110

Phe Ala Gln Tyr Gly Asp Asp Trp Arg Glu Met Arg Lys Leu Ala Met
        115                 120                 125

Leu Glu Leu Phe Ser Ser Lys Lys Leu Lys Ala Phe Arg Tyr Ile Arg
    130                 135                 140

Glu Glu Glu Ser Glu Val Leu Val Asn Lys Leu Ser Lys Ser Ala Glu
145                 150                 155                 160

Thr Arg Thr Met Val Asp Leu Arg Lys Ala Leu Phe Ser Tyr Thr Ala
                165                 170                 175

Ser Ile Val Cys Arg Leu Ala Phe Gly Gln Asn Phe His Glu Cys Asp
            180                 185                 190

Phe Val Asp Met Asp Lys Val Glu Asp Leu Val Leu Glu Ser Glu Thr
        195                 200                 205

Asn Leu Gly Ser Phe Ala Phe Thr Asp Phe Phe Pro Ala Gly Leu Gly
    210                 215                 220

Trp Val Ile Asp Arg Ile Ser Gly Gln His Ser Glu Leu His Lys Ala
225                 230                 235                 240

Phe Ala Arg Leu Ser Asn Phe Phe Gln His Val Ile Asp Asp His Leu
                245                 250                 255

Lys Pro Gly Gln Ser Gln Asp His Ser Asp Ile Ile Gly Val Met Leu
            260                 265                 270

Asp Met Ile Asn Lys Glu Ser Lys Val Gly Ser Phe Gln Val Thr Tyr
        275                 280                 285

Asp His Leu Lys Gly Val Met Ser Asp Val Phe Leu Ala Gly Val Asn
    290                 295                 300

Ala Gly Ala Ile Thr Met Ile Trp Ala Met Thr Glu Leu Ala Arg His
305                 310                 315                 320

Pro Arg Val Met Lys Lys Leu Gln Gln Glu Ile Arg Glu Ile Leu Gly
                325                 330                 335

Asp Asn Lys Glu Lys Ile Thr Glu Gln Asp Leu Glu Lys Val His Tyr
```

-continued

```
                    340                 345                 350
Leu Lys Leu Val Ile Glu Glu Thr Phe Arg Leu His Pro Pro Ala Pro
        355                 360                 365
Leu Leu Leu Pro Arg Glu Thr Met Ser Asp Leu Lys Ile Gln Gly Tyr
        370                 375                 380
Asn Ile Pro Lys Asn Thr Met Ile Glu Ile Asn Thr Tyr Ser Ile Gly
385                 390                 395                 400
Arg Asp Pro Asn Cys Trp Glu Asn Pro Asn Asp Phe Asn Pro Glu Arg
                405                 410                 415
Phe Ile Asp Ser Pro Val Glu Tyr Lys Gly Gln His Tyr Glu Leu Leu
            420                 425                 430
Pro Phe Gly Ala Gly Arg Arg Ile Cys Pro Gly Met Ala Thr Gly Ile
            435                 440                 445
Thr Ile Val Glu Leu Gly Leu Leu Asn Val Leu Tyr Phe Phe Asp Trp
        450                 455                 460
Ser Leu Pro Asp Gly Met Lys Ile Glu Asp Ile Asp Met Glu Glu Ala
465                 470                 475                 480
Gly Ala Phe Val Val Ala Lys Lys Val Pro Leu Glu Leu Ile Pro Thr
                485                 490                 495
Pro His Gln Trp
        500

<210> SEQ ID NO 3
<211> LENGTH: 438
<212> TYPE: PRT
<213> ORGANISM: Arabidopsis thaliana
<220> FEATURE:
<221> NAME/KEY: PEPTIDE
<222> LOCATION: (1)...(438)
<223> OTHER INFORMATION: Ceres Seq ID no. 2158132

<400> SEQUENCE: 3

Met Phe Leu His Phe Gly Val Val Pro Val Val Val Ser Thr Arg
 1               5                  10                  15
Glu Ala Ala Glu Glu Val Leu Lys Thr His Asp Leu Glu Thr Cys Thr
                20                  25                  30
Arg Pro Lys Leu Thr Ala Thr Lys Leu Phe Ser Tyr Asn Tyr Lys Asp
            35                  40                  45
Ile Gly Phe Ala Gln Tyr Gly Asp Asp Trp Arg Glu Met Arg Lys Leu
        50                  55                  60
Ala Met Leu Glu Leu Phe Ser Ser Lys Lys Leu Lys Ala Phe Arg Tyr
65                  70                  75                  80
Ile Arg Glu Glu Ser Glu Val Leu Val Asn Lys Leu Ser Lys Ser
                85                  90                  95
Ala Glu Thr Arg Thr Met Val Asp Leu Arg Lys Ala Leu Phe Ser Tyr
                100                 105                 110
Thr Ala Ser Ile Val Cys Arg Leu Ala Phe Gly Gln Asn Phe His Glu
            115                 120                 125
Cys Asp Phe Val Asp Met Asp Lys Val Glu Asp Leu Val Leu Glu Ser
        130                 135                 140
Glu Thr Asn Leu Gly Ser Phe Ala Phe Thr Asp Phe Pro Ala Gly
145                 150                 155                 160
Leu Gly Trp Val Ile Asp Arg Ile Ser Gly Gln His Ser Glu Leu His
                165                 170                 175
Lys Ala Phe Ala Arg Leu Ser Asn Phe Phe Gln His Val Ile Asp Asp
            180                 185                 190
```

```
His Leu Lys Pro Gly Gln Ser Gln Asp His Ser Asp Ile Ile Gly Val
        195                 200                 205

Met Leu Asp Met Ile Asn Lys Glu Ser Lys Val Gly Ser Phe Gln Val
    210                 215                 220

Thr Tyr Asp His Leu Lys Gly Val Met Ser Asp Val Phe Leu Ala Gly
225                 230                 235                 240

Val Asn Ala Gly Ala Ile Thr Met Ile Trp Ala Met Thr Glu Leu Ala
                245                 250                 255

Arg His Pro Arg Val Met Lys Lys Leu Gln Gln Glu Ile Arg Glu Ile
                260                 265                 270

Leu Gly Asp Asn Lys Glu Lys Ile Thr Glu Gln Asp Leu Glu Lys Val
            275                 280                 285

His Tyr Leu Lys Leu Val Ile Glu Glu Thr Phe Arg Leu His Pro Pro
        290                 295                 300

Ala Pro Leu Leu Leu Pro Arg Glu Thr Met Ser Asp Leu Lys Ile Gln
305                 310                 315                 320

Gly Tyr Asn Ile Pro Lys Asn Thr Met Ile Glu Ile Asn Thr Tyr Ser
                325                 330                 335

Ile Gly Arg Asp Pro Asn Cys Trp Glu Asn Pro Asn Asp Phe Asn Pro
                340                 345                 350

Glu Arg Phe Ile Asp Ser Pro Val Glu Tyr Lys Gly Gln His Tyr Glu
            355                 360                 365

Leu Leu Pro Phe Gly Ala Gly Arg Arg Ile Cys Pro Gly Met Ala Thr
        370                 375                 380

Gly Ile Thr Ile Val Glu Leu Gly Leu Leu Asn Val Leu Tyr Phe Phe
385                 390                 395                 400

Asp Trp Ser Leu Pro Asp Gly Met Lys Ile Glu Asp Ile Asp Met Glu
                405                 410                 415

Glu Ala Gly Ala Phe Val Val Ala Lys Lys Val Pro Leu Glu Leu Ile
            420                 425                 430

Pro Thr Pro His Gln Trp
        435

<210> SEQ ID NO 4
<211> LENGTH: 378
<212> TYPE: PRT
<213> ORGANISM: Arabidopsis thaliana
<220> FEATURE:
<221> NAME/KEY: PEPTIDE
<222> LOCATION: (1)...(378)
<223> OTHER INFORMATION: Ceres Seq. ID no. 2158133

<400> SEQUENCE: 4

Met Arg Lys Leu Ala Met Leu Glu Leu Phe Ser Ser Lys Lys Leu Lys
1               5                   10                  15

Ala Phe Arg Tyr Ile Arg Glu Glu Glu Ser Glu Val Leu Val Asn Lys
                20                  25                  30

Leu Ser Lys Ser Ala Glu Thr Arg Thr Met Val Asp Leu Arg Lys Ala
            35                  40                  45

Leu Phe Ser Tyr Thr Ala Ser Ile Val Cys Arg Leu Ala Phe Gly Gln
        50                  55                  60

Asn Phe His Glu Cys Asp Phe Val Asp Met Asp Lys Val Glu Asp Leu
65                  70                  75                  80

Val Leu Glu Ser Glu Thr Asn Leu Gly Ser Phe Ala Phe Thr Asp Phe
                85                  90                  95
```

-continued

```
Phe Pro Ala Gly Leu Gly Trp Val Ile Asp Arg Ile Ser Gly Gln His
            100                 105                 110
Ser Glu Leu His Lys Ala Phe Ala Arg Leu Ser Asn Phe Gln His
        115                 120                 125
Val Ile Asp Asp His Leu Lys Pro Gly Gln Ser Gln Asp His Ser Asp
    130                 135                 140
Ile Ile Gly Val Met Leu Asp Met Ile Asn Lys Glu Ser Lys Val Gly
145                 150                 155                 160
Ser Phe Gln Val Thr Tyr Asp His Leu Lys Gly Val Met Ser Asp Val
                165                 170                 175
Phe Leu Ala Gly Val Asn Ala Gly Ala Ile Thr Met Ile Trp Ala Met
            180                 185                 190
Thr Glu Leu Ala Arg His Pro Arg Val Met Lys Lys Leu Gln Gln Glu
        195                 200                 205
Ile Arg Glu Ile Leu Gly Asp Asn Lys Glu Lys Ile Thr Glu Gln Asp
    210                 215                 220
Leu Glu Lys Val His Tyr Leu Lys Leu Val Ile Glu Glu Thr Phe Arg
225                 230                 235                 240
Leu His Pro Pro Ala Pro Leu Leu Leu Pro Arg Glu Thr Met Ser Asp
                245                 250                 255
Leu Lys Ile Gln Gly Tyr Asn Ile Pro Lys Asn Thr Met Ile Glu Ile
            260                 265                 270
Asn Thr Tyr Ser Ile Gly Arg Asp Pro Asn Cys Trp Glu Asn Pro Asn
        275                 280                 285
Asp Phe Asn Pro Glu Arg Phe Ile Asp Ser Pro Val Glu Tyr Lys Gly
    290                 295                 300
Gln His Tyr Glu Leu Leu Pro Phe Gly Ala Gly Arg Arg Ile Cys Pro
305                 310                 315                 320
Gly Met Ala Thr Gly Ile Thr Ile Val Glu Leu Gly Leu Leu Asn Val
                325                 330                 335
Leu Tyr Phe Phe Asp Trp Ser Leu Pro Asp Gly Met Lys Ile Glu Asp
            340                 345                 350
Ile Asp Met Glu Glu Ala Gly Ala Phe Val Val Ala Lys Lys Val Pro
        355                 360                 365
Leu Glu Leu Ile Pro Thr Pro His Gln Trp
    370                 375
```

What is claimed is:

1. An isolated polynucleotide having a cDNA sequence that encodes a polypeptide, wherein the amino acid sequence of said polypeptide has the sequence set forth in SEQ ID NO:2.

* * * * *